(12) United States Patent
Megerle

(10) Patent No.: US 6,610,977 B2
(45) Date of Patent: Aug. 26, 2003

(54) SECURITY SYSTEM FOR NBC-SAFE BUILDING

(75) Inventor: Clifford Megerle, Manassas, VA (US)

(73) Assignee: Lockheed Martin Corporation, Bethesda, MD (US)

(*) Notice: Subject to any disclaimer, the term of this patent is extended or adjusted under 35 U.S.C. 154(b) by 53 days.

(21) Appl. No.: 09/969,050

(22) Filed: Oct. 1, 2001

(65) Prior Publication Data

US 2003/0085348 A1 May 8, 2003

(51) Int. Cl.[7] ............................................. G01N 23/00
(52) U.S. Cl. .................. 250/287; 250/286; 73/23.2; 73/28.01; 73/23; 73/23.36; 378/88; 378/86; 378/186
(58) Field of Search ................................. 250/287, 286; 73/23.2, 28.01, 23, 23.36; 378/85, 86, 186

(56) References Cited

U.S. PATENT DOCUMENTS

| | | |
|---|---|---|
| 4,987,767 A | 1/1991 | Corrigan et al. |
| 5,047,723 A | 9/1991 | Puumalainen |
| 5,109,691 A | 5/1992 | Corrigan et al. |
| 5,311,166 A | 5/1994 | Frye |
| 5,692,029 A | 11/1997 | Husseiny et al. |
| 5,692,446 A | 12/1997 | Becker et al. |
| 5,866,430 A | 2/1999 | Grow |
| 5,915,268 A | 6/1999 | Linker et al. |
| 5,965,882 A | 10/1999 | Megerle et al. |
| 6,073,499 A | 6/2000 | Settles |
| 6,100,698 A | 8/2000 | Megerle et al. |

OTHER PUBLICATIONS

U.S. Pub: 2003/0009661 A1, "Security System and Method of Security Service Business", Tsutsumi et al. (Jan. 9, 2003).*

* cited by examiner

Primary Examiner—John R. Lee
Assistant Examiner—Zia R. Hashmi
(74) Attorney, Agent, or Firm—Simpson & Simpson, PLLC

(57) ABSTRACT

A method and apparatus for screening an object for the presence of an explosive, chemical warfare agent, biological warfare agent, drug, metal, weapon, and/or radioactive material. The apparatus includes a portal through which the object is arranged to pass, the portal including a housing equipped with an ion mobility spectrometer and a surface acoustic wave device for detecting explosives, drugs and chemical warfare agents. In another embodiment the housing is equipped with a biological warfare agent detector, chemical warfare agent detector, metal detector, x-ray system, and/or radiation detector.

60 Claims, 15 Drawing Sheets

SECURITY SYSTEM FOR NBC-SAFE BUILDING

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of Contract No. MDA972-99-3-0029 awarded by DARPA.

FIELD OF THE INVENTION

The present invention relates generally to security systems and, more particularly, to a security system for NBC-safe buildings.

BACKGROUND OF THE INVENTION

Physical security for NBC-safe buildings requires that no entering personnel, packages or vehicles carry weapons, explosives, chemical warfare agents, or biological warfare agents. Unfortunately, heretofore, no convenient, single-point inspection system containing sensors for all of these classes of threats has existed.

A possible reason for the lack of such a single-point inspection system is the breadth and variety of the possible threatening agents and devices, and the corresponding number and variety of necessary sensing, detection and identification apparatus necessary to implement such a unified system, as well as the problem of an effective methodology for detecting such a wide variety of threats. To better understand the problem to be solved, it is useful to understand and appreciate the various types of threats and agents at issue. We therefore begin with a general discussion of these various types/classes of threats:

Biological Warfare Agents

The phrase "biological warfare agents" as used in this patent refers generally to toxins, bioregulators, and biological warfare organisms. These agents, in turn, are described as follows:

Toxins

Toxins are poisons produced by living organisms. They are extremely poisonous and generally have a toxicity several orders of magnitude greater than nerve agents. Cytotoxins (such as ricin) cause cellular destruction, whereas neurotoxins affect the central nervous system.

Bioregulators

Bioregulators are substances related to those normally found in the body that regulate certain body functions and processes. Some bioregulator agents influence blood pressure, others cause pain. An example of a bioregulator is Substance P which causes a rapid loss of blood pressure.

Biological Warfare Organisms

Biological warfare organisms, as opposed to chemical agents or toxins, are, by definition, alive. These organisms include viruses, bacteria, rickettsia, and fungi. All of them are capable of genetic engineering, which can make them more virulent, less treatable, and more difficult to detect.

Known virus warfare organisms include, but are not limited to, variola virus, Venezuelan equine encephalitis virus, dengue virus, hantavirus, Marburg virus, Ebola virus, Crimean Congo hemorrhagic fever virus, and arenaviruses.

Known bacteria warfare organisms include, but are not limited to, bacillus *anthracis, clostridium botulinum, francisella tularensis*, brucella, *vibrio cholerae, chlamydia psittaci, shigella dysenteriae, staphylococcus aureus, yersinia pestis, burkholderia mallei*, and *salmonella typhi*.

Chemical Warfare Agents

Chemical warfare agents include, but are not limited to: blister agents (e.g., Mustards and Lewisite), nerve agents (e.g., Sarin, VX, Tabun and Soman)), arsenicals, the G-agents, and blood agents (cyanides). More particularly, chemical warfare agents further include, but are not limited to: GF, Mustard-Lewisite HL, Levinstein Mustard H, Nitrogen Mustards HN-1, HN-2, HN-3, Mustard-T mixture HT, Acrolein, Cyanogen Chloride CK, Chloropicrin, Chlorosulfonic acid, Diphosgene, Chlorine, Phosgene Oxime (CX), Phosgene (CG), Ethyldichoroarsine (ED), Ethyldibromoarsine, Diphenylchloroarsine (DA), Diphenylcyanarsine (DC), Ethylbromoacetate, Ethyliodoacetate, Ethylacetate, Bromoacetone, Chloroacetone, Benzylbromide, Xylylbromide, Sodiumdichloroicocyanate. This, of course, is but a partial representative list.

Weapons

For purposes of this patent, a "weapon" is defined to be any object or substance designed to inflict a wound, cause injury, or incapacitate, including, but not limited to, all firearms, BB guns, air guns, pellet guns, knives (including switchblade knives), axes, brass knuckles, swords, staffs, bos, ninja weapons, escrima sticks, sai, kama, whips, chains, shinai, tonfa, nunchaku, blowguns, slingshots, and crossbows. It should be appreciated that this is only a partial list.

Explosives

Explosives are compounds capable of rapid decomposition with generation of high heat and a large quantity of gaseous product giving rise to a shock wave. The first recognized explosive was gunpowder which generally consists of a mix of potassium nitrate (75%), charcoal (10%) and sulphur (10%). The next major advancement was the discovery of nitroglycerine in 1846 by Ascanio Sobreo. Alfred Noble later mixed nitroglycerine with silica to make the more stable compound dynamite.

There are generally four main groups of explosives: Primary, Low, High and Blasting Agents. For purposes of this patent, the term "explosive" includes explosives, blasting agents, and detonators. It further includes, but is not limited to:

Primary Explosives

Lead Azide—primary explosive used mainly as a detonator in blasting caps and fuse detonators.

Lead Styphnate—primary explosive used mainly as a detonator in blasting caps.

Mercury gulminate—primary explosive used mainly as a detonator.

Low Explosives

Gunpowder—low explosive used as a propellant.

Fireworks—low explosive used as a propellant.

High Explosives

RDX—high explosive made of nitric acid and hexamethylene-tetramine often used in bombs as a primer or booster.

TNT—high explosive made of trintro-totoluene and is the most widely used military explosive in the world. TNT is used alone or in combination with other explosives as a main charge in artillery projectiles, mortar rounds, and aerial bombs.

Pentolite (PETN+TNT)—high explosive made of Pentaerythritol tretrinitrate often used in detonating caps and fuses.

Nitroglycerin—high explosive which is frequently used in dynamite.

Blasting Agents

A blasting agent is any material or mixture, consisting of fuel and oxidizer, that is intended for blasting and not otherwise defended as an explosive; if the finished product, as mixed for use or shipment, cannot be detonated by means of a number 8 test blasting cap when unconfined. A number 8 test blasting cap is one containing 2 grams of a mixture of 80 percent mercury fulminate and 20 percent potassium chlorate, or a blasting cap of equivalent strength. An equivalent strength cap comprises 0.40–0.45 grams of PETN base charge pressed in an aluminum shell with bottom thickness not to exceed to 0.03 of an inch, to a specific gravity of not less than 1.4 g/cc., and primed with standard weights of primer depending on the manufacturer. Examples of well known blasting agents include, but are not limited to:

Dynamite—blasting agent which is a mixture of nitroglycerin and kieselguhr often used for blasting and tunneling.

ANFO—blasting agent made of ammonium nitrate (commercial fertilizer) and fuel oils often used for excavating and vehicle bombs.

Plastic Explosives

A plastic explosive is defined as "an explosive material in flexible or elastic sheet form formulated with one or more high explosives which in their pure form has a vapor pressure less than $10^{-4}$ Pa at a temperature of 25° C., is formulated with a binder material, and is as a mixture malleable or flexible at normal room temperature." 18 U.S.C. 841(q); 27 CFR 55.180(d)(4). The present invention is designed to test for C-4 and Semtex, among other plastic explosives.

Under federal law, all plastic explosives manufactured or imported on or after Apr. 24, 1996, must contain a detection agent. Federal law enforcement agencies and the military may possess unmarked plastic explosives if they meet the requirements of the 15-year use-up period described in 18 U.S.C. 842(n); 27 CFR 55.180(c). These detection agents, when introduced into a plastic explosive or formulated in such explosive as a part of the manufacturing process in such a manner as to achieve homogeneous distribution in the finished explosive, include:

(1) Ethylene glycol dinitrate (EGDN), C[2]H[4](NO[3])[2], molecular weight 152, when the minimum concentration in the finished explosive is 0.2 percent by mass;

(2) 2,3-Dimethyl-2,3-dinitrobutane (DMNB), C[6]H[12](NO[2])[2], molecular weight 176, when the minimum concentration in the finished explosive is 0.1 percent by mass;

(3) Para-Mononitrotoluene (p-MNT), C[7]H[7]NO[2], molecular weight 137, when the minimum concentration in the finished explosive is 0.5 percent by mass;

(4) Ortho-Mononitrotoluene (o-MNT), C[7]H[7]NO[2], molecular weight 137, when the minimum concentration in the finished explosive is 0.5 percent by mass; and, (5) any other substance set forth in the table in part 2 of the Technical Annex to the Convention on the Marking of Plastic Explosives (18 U.S.C. Chapter 40).

Partial List of Explosive Materials

Pursuant to the provisions of section 841(d) of title 18, U.S.C., and 27 CFR 55.23, the Director, Bureau of Alcohol, Tobacco and Firearms, must revise and publish in the Federal Register at least annually a list of explosives determined to be within the coverage of 18 U.S.C. Chapter 40. This chapter covers not only explosives, but also blasting agents and detonators, all of which are defined as explosive materials in section 841(c) of title 18, U.S.C. This list is incorporated herein by reference, and is reprinted herebelow. The list is intended to include any and all mixtures containing any of the materials on the list. Materials containing blasting agents are marked by an asterisk. While the list is comprehensive, it is not all-inclusive. The fact that an explosive material may not be on the list does not mean that it is not within the scope of coverage of the appended claims. Explosive materials are listed alphabetically by their common names, followed by chemical names and synonyms in brackets.

| List of Explosive Materials | |
|---|---|
| A | M |
| Acetylides of heavy metals. | Magnesium ophorite explosives. |
| Aluminum containing polymeric propellant. | Mannitol hexanitrate. |
| Aluminum ophorite explosive. | MDNP [methyl 4,4-dinitropentanoate]. |
| Amatex. | MEAN [monoethanolamine nitrate]. |
| Amatol. | Mercuric fulminate. |
| Ammonal. | Mercury oxalate. |
| Ammonium nitrate explosive mixtures (cap sensitive). | Mercury tartrate. |
| | Metriol trinotrate. |
| *Ammonium nitrate explosive mixtures (non cap sensitive). | Minol-2 [40% TNT, 40% ammonium nitrate, 20% aluminum]. |
| Aromatic nitro-compound explosive mixtures. | MMAN [monomethylamine nitrate]; methylamine nitrate. |
| Ammonium perchlorate explosive mixtures. | Mononitrotoluene-nitroglycerin mixture. |
| Ammonium perchlorate composite propellant. | Monopropellants. |
| Ammonium picrate [picrate of ammonia, Explosive D]. | N |
| Ammonium salt lattice with isomorphously substituted inorganic salts. | NIBTN [nitroisobutametriol trinitrate]. |
| *ANFO [ammonium nitrate-fuel oil]. | Nitrate sensitized with gelled nitroparaffin. |
| | Nitrated carbohydrate explosive. |
| | Nitrated glucoside explosive. |
| B | Nitrated polyhydric alcohol explosives. |
| | Nitrates of soda explosive mixtures. |
| Baratol. | Nitric acid and a nitro aromatic compound |

-continued

List of Explosive Materials

Baronol.
BEAF [1,2-bis (2,2-difluoro-2-nitroacetoxyethane)].
Black powder.
Black powder based explosive mixtures.
*Blasting agents, nitro-carbo-nitrates, including non cap sensitive slurry and water gel explosives.
Blasting caps.
Blasting gelatin.
Blasting powder.
BTNEC [bis (trinitroethyl) carbonate].
Bulk salutes.
BTNEN [bis (trinitroethyl) nitramine].
BTTN [1,2,4 butanetriol trinitrate].
Butyl tetryl.

C

Calcium nitrate explosive mixture.
Cellulose hexanitrate explosive mixture.
Chlorate explosive mixtures.
Composition A and variations.
Composition B and variations.
Composition C and variations.
Copper acetylide.
Cyanuric triazide.
Cyclotrimethylenetrinitramine [RDX].
Cyclotetramethylenetetranitramine [HMX].
Cyclonite [RDX].
Cyclotol.

D

DATB [diaminotrinitrobenzene].
DDNP [diazodinitrophenol].
DEGDN [diethyleneglycol dinitrate].
Detonating cord.
Detonators.
Dimethylol dimethyl methane dinitrate composition.
Dinitroethyleneurea.
Dinitroglycerine [glycerol dinitrate].
Dinitrophenol.
Dinitrophenolates.
Dinitrophenyl hydrazine.
Dinitroresorcinol.
Dinitrotoluene-sodium nitrate explosive mixtures.
DIPAM.
Dipicryl sulfone.
Dipicrylamine.
Display fireworks.
DNPD [dinitropentano nitrile].
DNPA [2,2-dinitropropyl acrylate].
Dynamite.

E

EDDN [ethylene diamine dinitrate].
EDNA.
Ednatol.
EDNP [ethyl 4,4-dinitropentanoate].
Erythritol tetranitrate explosives.
Esters of nitro-substituted alcohols.
EGDN [ethylene glycol dinitrate].
Ethyl-tetryl.
Explosive conitrates.
Explosive gelatins.
Explosive mixtures containing oxygen-releasing inorganic salts and hydrocarbons.
Explosive mixtures containing oxygen-releasing inorganic salts and nitro bodies.
Explosive mixtures containing oxygen-releasing inorganic salts and water insoluble fuels.
Explosive mixtures containing oxygen-releasing inorganic salts and water soluble fuels.

explosive.
Nitric acid and carboxylic fuel explosive.
Nitric acid explosive mixtures.
Nitro aromatic explosive mixtures.
Nitro compounds of furane explosive mixtures.
Nitrocellulose explosive.
Nitroderivative of urea explosive mixture.
Nitrogelatin explosive.
Nitrogen trichloride.
Nitrogen tri-iodide.
Nitroglycerine [NG, RNG, nitro, glyceryl trinitrate, trinitroglycerine].
Nitroglycide.
Nitroglycol (ethylene glycol dinitrate, EGDN).
Nitroguanidine explosives.
Nitroparaffins Explosive Grade and ammonium nitrate mixtures.
Nitronium perchlorate propellant mixtures.
Nitrostarch.
Nitro-substituted carboxylic acids.
Nitrourea.

O

Octogen [HMX].
Octol [75 percent HMX, 25 percent TNT].
Organic amine nitrates.
Organic nitramines.

P

PBX [RDX and plasticizer].
Pellet powder.
Penthrinite composition.
Pentolite.
Perchlorate explosive mixtures.
Peroxide based explosive mixtures.
PETN [nitropentaerythrite, pentaerythrite tetranitrate, pentaerythritol tetranitrate].
Picramic acid and its salts.
Picramide.
Picrate of potassium explosive mixtures.
Picratol.
Picric acid (manufactured as an explosive).
Picryl chloride.
Picryl fluoride.
PLX [95% nitromethane, 5% ethylenediamine].
Polynitro aliphatic compounds.
Polyolpolynitrate-nitrocellulose explosive gels.
Potassium chlorate and lead sulfocyanate explosive.
Potassium nitrate explosive mixtures.
Potassium nitroaminotetrazole.
Pyrotechnic compositions.
PYX [2,6-bis(picrylamino)]-3,5-dinitropyridine.

R

RDX [cyclonite, hexogen, T4, cyclo-1,3,5,-trimethylene-2,4,6,-trinitramine; hexahydro-1,3,5-trinitro-S-triazine].

S

Safety fuse.
Salutes (bulk).
Salts of organic amino sulfonic acid explosive mixture.
Silver acetylide.
Silver azide.
Silver fulminate.
Silver oxalate explosive mixtures.
Silver styphnate.
Silver tartrate explosive mixtures.
Silver tetrazene.
Slurried explosive mixtures of water, -continued

| List of Explosive Materials | |
|---|---|
| Explosive mixtures containing sensitized nitromethane. | inorganic oxidizing salt, gelling agent, fuel, and sensitizer (cap sensitive). |
| Explosive mixtures containing tetranitromethane (nitroform). | Smokeless powder. |
| | Sodatol. |
| Explosive nitro compounds of aromatic hydrocarbons. | Sodium amatol. |
| | Sodium azide explosive mixture. |
| Explosive organic nitrate mixtures. | Sodium dinitro-ortho-cresolate. |
| Explosive liquids. | Sodium nitrate-potassium nitrate explosive mixture. |
| Explosive powders. | |
| | Sodium picramate. |
| F | Special fireworks. |
| | Squibs. |
| Flash powder. | Styphnic acid explosives. |
| Fulminate of mercury. | |
| Fulminate of silver. | T |
| Fulminating gold. | |
| Fulminating mercury. | Tacot [tetranitro-2,3,5,6-dibenzo-1,3a,4,6a tetrazapentalene]. |
| Fulminating platinum. | |
| Fulminating silver. | TATB [triaminotrinitrobenzene]. |
| | TEGDN [triethylene glycol dinitrate]. |
| G | Tetrazene [tetracene, tetrazine, 1(5-tetrazolyl)-4-guanyl tetrazene hydrate]. |
| Gelatinized nitrocellolose. | Tetranitrocarbazole. |
| Gem-dinitro aliphatic explosive mixtures. | Tetryl [2,4,6 tetranitro-N-methylaniline]. |
| Guanyl nitrosamino guanyl tetrazene. | Tetrytol. |
| Guanyl nitrosamino guanylidene hydrazine. | Thickened inorganic oxidizer salt slurried explosive mixture. |
| Guncotton. | |
| | TMETN [trimethylolethane trinitrate]. |
| H | TNEF [trinitroethyl formal]. |
| | TNEOC [trinitroethylorthocarbonate]. |
| Heavy metal azides. | TNEOF [trinitroethylorthoformate]. |
| Hexanite. | TNT [trinitrotoluene, trotyl, trilite, triton]. |
| Hexanitrodiphenylamine. | Torpex. |
| Hexanitrostilbene. | Tridite. |
| Hexogen (RDX). | Trimethylol ethyl methane trinitrate composition. |
| Hexogene or octogene and a nitrated N-methylaniline. | |
| Hexolites. | Trimethylolthane trinitrate-nitrocellulose. |
| HMX [cyclo-1,3,5,7-tetramethylene 2,4,6,8-tetranitramine; Octogen]. | Trimonite. |
| | Trinitroanisole. |
| Hydrazinium nitrate/hydrazine/aluminum explosive system. | Trinitrobenzene. |
| | Trinitrobenzoic acid. |
| Hydrazoic acid. | Trinitrocresol. |
| | Trinitro-meta-cresol. |
| I | Trinitronaphthalene. |
| | Trinitrophenetol. |
| Igniter cord. | Trinitrophloroglucinol. |
| Igniters. | Trinitroresorcinol. |
| Initiating tube systems. | Tritonal. |
| K | U |
| KDNBF [potassium dinitrobenzo-furoxane]. | Urea nitrate. |
| L | W |
| Lead azide. | Water-bearing explosives having salts of oxidizing acids and nitrogen bases, sulfates, or sulfamates (cap sensitive). |
| Lead mannite. | |
| Lead mononitroresorcinate. | |
| Lead picrate. | Water-in-oil emulsion explosive compositions. |
| Lead salts, explosive. | |
| Lead styphnate [styphnate of lead, lead trinitroresorcinate]. | X |
| Liquid nitrated polyol and trimethylolethane. | Xanthamonas hydrophilic colloid explosive mixture. |
| Liquid oxygen explosives. | |

Nuclear Weapons & Mateials

Discoveries in the 1930's of the fissioning (splitting) of atoms, also known as nuclear fission, laid the groundwork for the development in the 1940's of nuclear weapons. Nuclear fission, in which an atomic nucleus splits into fragments, usually two fragments of comparable mass, with the evolution of approximately 100 million to several hundred million electron volts of energy, lead to the production of nuclear fission devices that are used to ignite thermonuclear reactions. Types of nuclear weapons which cause thermonuclear reactions, for purposes of this patent, include, but are not limited to, atomic and hydrogen bombs, nuclear and conventional warheads.

One element that can be used in atomic bombs is Uranium-235 (U-235). U-235 is a heavy metal that has many more neutrons than protons that have the capacity to facilitate an explosion and releases a powerful form of lethal radioactivity. Another element that can be used for making atomic bombs is Plutonium, in its isotope Pu-239 form. Pu-239 is not fissionable in and of itself, but may act as a catalyst to the greater reaction occurring in an atomic bomb. A bomb made with Pu-239 basically works with a detonating head which starts off an explosive chain reaction.

Another type of nuclear weapon, which is thousands of times more powerful than an atomic bomb, is the hydrogen bomb. Working on a different physical principle known as nuclear fusion, a common hydrogen bomb has the power of up to 10 megatons, compared to the atomic bomb that was dropped on Hiroshima, Japan in 1945, which had the power of 13 kilotons. Nuclear fusion only can happen under very hot conditions and the explosion of an atomic bomb attached to a hydrogen bomb provides the heat necessary to start fusion. This type of nuclear weapon has never been used in warfare, however there have been underwater hydrogen bomb tests.

Nuclear missiles, for purposes of this patent, which carry nuclear warheads, are another type of nuclear weapon. The cruise or ballistic missiles are sometimes referred to as delivery missiles and may contain, inter alia, motors, guidance systems and warheads. There are land-based missiles, air-to-surface missiles and bombers, and sea-launched missiles to name a few. Compared to atomic or hydrogen bombs, also known as free-falling bombs, delivery missiles increase the explosive power of a nuclear weapon by being fired, thrown, dropped or otherwise projected at a target from a tube or silo. Land-based missiles are more mobile than air-to-surface missiles, and can be mounted on transporters along with firing and control facilities.

Ballistic missiles follow a ballistic, or unguided, trajectory, similar to an artillery shell after the powered boost phase. These missiles may undergo later minor corrections in mid-course or during reentry from space. Cruise missiles fly like small aircraft and may take a preset but devious course to the target at low altitude. Either of these missiles can be launched or delivered from parachutes, submarines, surface ships, underground launch-tubes, or from aircraft.

Although certain nuclear bombs and weapons are quite large, it is possible to transport some nuclear bombs and weapons, as well as radioactive material used to make these weapons and bombs, on trucks and similar vehicles.

METHODS OF DETECTION

Chemical Warfare Agents

The history of chemical agent analysis dates back to the 17$^{th}$ century. The development of U.S. Army detectors, alarms, and warning systems dates back to World War I when chemical warfare was first introduced on a large scale.

When the United States entered World War I in April, 1917, chemists in laboratories had the ability to identify chemical agents, but the U.S. Army had no ability to detect chemical agents either as vapor or on surfaces in the field. Instead, the American soldier on the chemical battlefield had to rely on his own senses (smell, and throat and nose irritation) to detect chemicals. Since most of the World War I chemical agents had identifiable unique odors, the sense of smell was the best detector of the presence of chemical agents. For example, troops learned that German mustard agent smelled like mustard, while allied mustard agent smelled like garlic. One of the earliest detection methods was the so-called "sniff test", where a soldier would pull the edge of his gas mask away from his face to allow outside air to enter the mask. Unfortunately, the sniff test was inaccurate for low levels of chemical vapor and, after several hours of "sniff testing" a soldier would gradually lose his ability to detect low levels of mustard agent. Of course, the sniff test was extremely dangerous in high levels of mustard agent.

During the war, numerous efforts were made to improve chemical and biological detection. Early apparatus included vapor field detectors, such as the copper flame test lantern, the selenious acid field detector, the iodine pentoxide test, the iodic acid test field detector, and the hydrogen sulfide field detector. None of these detectors were perfected before the end of World War I. Animals such as dogs, pigeons, and canaries were also used to alert soldiers to the presence of toxic chemical agents, and, interestingly, snails and slugs were used with some degree of effectiveness.

To meet the unfulfilled need for effective chemical warfare detection, in 1934 the Chemical Warfare Service prepared a military requirement for a chemical agent detector that could detect with great rapidity the presence of one chemical agent in the atmosphere, primarily mustard gas, in the presence of other chemical gases. This requirement was not met until World War II (1942), when the M4 HS Vapor Detector Kit was standardized. This detector used a reagent, DB3, which reacted with mustard to give an intense color change. Other detection means were also developed and used during the war, including liquid detector paint, liquid detector paper, detector crayons, and various types of chemical agent detector kits. After the war, in the 1950s, the M9A2 chemical agent detector kit was standardized, the first standardized kit to have the capability of detecting nerve agents (G-agents). Water and food testing kits were also standardized during the 1950s. In the late 1950s, the first automatic detector/alarm apparatus were standardized.

In The 1960s and 1970s, improvements continued to be made in chemical detectors, particularly field detectors. The M151A1 chemical agent detector kit could detect both G- and V-agents, in addition to mustard agent, cyanogen chloride (CK) and phosgene oxime (CX). Improvements were also made during this time in chemical agent detection paper and sampling and analyzing kits. In the 1980s, the military standardized the Chemical Agent Monitor (CAM), a lightweight hand-held chemical detector for monitoring chemical contamination. This device detected vapors by sensing molecular ions of specific mobilities and used timing and microprocessor techniques to reject interferences.

In 1995, the M21 Remote Sensing Chemical Agent Alarm was standardized. The M21 was an automatic scanning, passive infrared sensor which detected nerve and blister agent vapor clouds based on changes in the background infrared spectra caused by the presence of agent vapor.

As of the filing of the application for this patent, a representative state of the art detector is the M90-D1-A chemical warfare agent detector, manufactured by Environics Oy of Finland. This detector uses hybrid detection technology. Its main sensor is an aspiration type ion mobility spectrometer, and its secondary sensor uses semiconductor technology. The manufacturer boasts that this detector can recognize "all known chemical warfare agents", such as nerve, blister and blood agents.

Explosives Trace Detection Equipment and Technologies

Explosive trace detection equipment and technologies is best described in Chapter 2 of "Survey of Commercially Available Explosives Detection Technologies and Equipment", Sandia National Laboratories, published by the National Law Enforcement and Corrections Technology Center, September 1998, reprinted herebelow in its entirety:

"The technologies and equipment presented in this section represent the state-of-the-art, commercially available explosives trace detection equipment. The term trace refers to both vapor and particulate sampling of the explosives. The distinction made here is that trace detection equipment is passive in that it only detects the vapors or microscopic particles emitted from the explosives compared to an active interrogator, or bulk detecting system, which uses a source of radiation (x-rays, gamma rays, radio frequencies, or magnetic field) to stimulate a response from explosives. In addition, a discussion of personnel portals, some of which are still in the prototype and testing stage of development, is included.

Prior to acquiring an appreciation for the capabilities of some of the present-day explosives detection systems, some understanding of the detection problem is needed. The principal problem in the detection of explosive vapors is the very low vapor pressures of some of the explosives of interest, which directly relate to the amount of explosive available in the air to collect as a vapor sample. The compound EGDN (ethylene glycol dinitrate), the most vaporous compound in nitrated dynamite, has a vapor pressure of 64 parts per million (1 PPM is 1 part in $10^6$ parts of air). TNT has a vapor pressure of 6 parts per billion (6 parts in $10^9$ parts of air). PETN (pentaerythritol tetranitrate) and RDX (cyclonite) are the explosive components found in Detasheet® and C-4, respectively, and have a vapor pressure of 6 parts per trillion (6 parts in $10^{12}$ parts of air), which is analogous to 6 seconds in 32,000 years. These vapor pressure numbers are for saturated head space vapor. In other words, if the explosive were confined in an airtight container at room temperature and allowed to equilibrate, thereby coating all available surfaces (the required times for the various explosives to reach this equilibrium state will vary), the resulting undisturbed vapor pressures are the numbers reported above. In real-world situations, with uncontrolled air currents, temperature fluctuations, etc., the actual vapor pressure can be orders of magnitude less. This property combines with others such as high electronegativity, thermal instability, and a high affinity for adsorbents (stickiness), to present a real challenge in the successful detection of these molecules.

Detection Technologies
Electron-Capture Detector (ECD)

The electron-capture detector (ECD) is an ionization chamber in which electrons are produced from a radioactive cathode, usually tritium or nickel-63. These electrons are injected into a stream of inert carrier gas (helium or argon), where they lose their energy by inelastic collisions with the carrier gas molecules and become thermalized. These thermal electrons are collected by an anode that produces a constant (standing) current. When an electron-capturing compound (such as an explosive) is introduced into the carrier gas, the standing current is reduced. ECDs have a fast response, a sensitivity of about 1 ppb for most electron-capturing compounds, and are comparatively low in cost. However, the ECD is not compound specific, i.e., it cannot tell with certainty what type of electron capturing compound is present. There are also some common nonexplosive substances that give rise to ECD signals, such as atmospheric oxygen, many substituted hydrocarbons such as FreonTM, fertilizers, and some household cleaners. In order to make the electron-capture detector more specific, some explosive detectors combine gas chromatography with ECD. In gas chromatography, components of volatile compounds are separated in a column containing a stationary phase, through which a stream of inert gas passes continuously. As the different compounds interact differently with the stationary phase, they emerge from the column at different retention times. The detection system looks at these retention times in conjunction with the ECD output and makes a determination of whether an explosive is present or not. The cost for an ECD-based explosives detection system is approximately $20,000.

Chemiluminescence

The chemiluminescence principle is based on the detection of infrared light emitted from electronically excited NO2*. The electronically excited NO2* results from the reaction of nitric oxide (NO) with ozone (O3). Most explosives contain NO2 groups that can be pyrolized to produce nitric acid. In a chemiluminescence detector, the ozone reaction generally takes place in an evacuated reaction chamber maintained at a pressure of about 3 torr. A photomultiplier situated behind a red light filter is used to detect the infrared light emitted from the NO2*. The red filter is in place to block any light with spectral frequency higher than the near infrared. The signal output from the photomultiplier is directly proportional to the amount of NO present in the reaction chamber. It is this signal that is used to detect the presence of explosives in a chemiluminescence system.

The chemiluminescence detector alone is not explosive type specific. Therefore, another technology, such as gas chromatography, needs to be used before the detector to selectively separate the explosive compounds for proper identification. Technical advances in high-speed gas chromatography make it possible to do the required separation of the explosive compounds and subsequent detection in less than 18 seconds.

Chemiluminescence technology is typically higher in cost than other explosives detection technologies (around $150,000), but has excellent sensitivity and selectivity when combined with high-speed gas chromatography. A wide range of explosives are detectable, including EGDN, NG (nitroglycerin), ANFO, TNT, DNT (dinitrotoluene), RDX, and PETN. No radioactive source is required for detector operation, and this may reduce both time and paperwork when transporting the system.

Ion Mobility Spectrometry (IMS)

Ion mobility spectrometry (IMS) was created between 1965 and 1970 from studies on ion-molecule chemistry at atmospheric or elevated pressure with mass spectrometers and from ionization detectors for airborne vapor monitoring. A conventional ion mobility spectrometer consists of two main areas: the reaction region and the drift region. In the reaction region, atmospheric pressure carrier gas (clean, dry air) is ionized by collision of beta particles from a weak nickel-63 source with nitrogen and oxygen. These reactant ions then undergo ion/molecule reactions with the explosive molecule. The explosive molecules also undergo other ion forming reactions such as adduct formation and dissociation reactions.

Under the influence of an electric field, the mixture of reactant and product ions reaches a shutter grid that separates the reaction region and the drift region. The shutter grid is made up of sets of thin mesh wires with a bias voltage between them. With the bias voltage applied, the ions are attracted to the gating grid and lose their charge. Then the grid bias is briefly turned off, and ions are transmitted into the drift region of the cell. The ions are then focused and accelerated by an electric field (typically 1,000 to 3,000 volts) along the drift region (typically 8 centimeters) to arrive at the collector electrode (typically in a time of 10 to 20 milliseconds). The smaller, compact ions have a higher mobility than the heavier ions, and therefore traverse the region and collide with the collector plate in a shorter time. The collector current is then amplified; its magnitude, as a function of time, is proportional to the number of ions arriving at that moment.

In an IMS explosives detection system, times required for ions of specific explosives to drift down the IMS tube are precisely known and are programmed into the system's microprocessor. The microprocessor monitors the collector electrode signal at the programmed drift times to detect the presence of explosive molecule ions. Typical analysis cycles require 5 to 8 seconds from introduction of sample to alarm notification.

Some systems combine IMS with a front-end gas chromatography (GC) in order to optimize selectivity.

Ion mobility spectrometry detection systems tend to be mid-range in price ($40,000 to $60,000), costing more than the ECD-based detectors but less than the chemiluminescence detectors. Limits of detection for most explosives are in the sub-nanogram range with few interferents known to give false alarms. IMS technology can also be applied to drug detection and the chemical/biological warfare (C/B) arena.

Several manufacturers presently offer drug detection as a standard or optional feature on their IMS detectors. Be aware that in many cases the unit must be powered down momentarily to switch between the drug and explosives detection modes. Future trends in IMS technology are to continue miniaturization of detection instruments and incorporate a nonradioactive ionization source.

Gas Chromatography/Surface Acoustic Wave (GC/SAW)

Another type of technology used for explosives detection utilizes a portable gas chromatograph (GC) equipped with a surface acoustic wave (SAW) detector. In a SAW-based GC system, the SAW resonator crystal is exposed to the exit gas of a GC capillary column by a carefully positioned and temperature-controlled nozzle. When condensable vapors entrained in the GC carrier gas impinge upon the active area between the resonator electrodes, a frequency shift occurs in proportion to the mass of the material condensing on the crystal surface. The frequency shift is dependent upon the properties (mass and the elastic constants) of the material being deposited, the temperature of the SAW crystal, and the chemical nature of the crystal surface.

A thermoelectric cooler maintains the SAW surface at sufficiently low temperatures to ensure a good trapping efficiency for explosive vapors. This cooler can be reversed to heat the crystal in order to clean the active surface (boil off adsorbed vapors). The temperature of the SAW crystal acts as a control over sensor specificity based upon the vapor pressure of the species being trapped. This feature is useful in distinguishing between relatively volatile materials and sticky explosive materials.

During a sampling sequence, vapor samples are drawn through the GC inlet from a preconcentrator and then pumped through a cryo-trap. The cryo-trap is a metal capillary tube held at a temperature low enough to trap explosive vapors, while allowing more volatile vapors to pass through. After passing through a second cryo-trap the sample is injected into the GC column and separated in time by normal column operation for species identification. As the constituent vapors exit the column, they are collected and selectively trapped on the surface of the SAW crystal, where the frequency shift can be correlated to the material concentration.

Total analysis time, including preconcentration of the vapors, is typically 10 to 15 seconds. Sensitivity to picogram levels of explosives has been shown by the manufacturer of the only commercially available system. The system is portable, about the size of a large briefcase. Cost is similar to an ECD system, and the system is operational within 10 minutes of setup.

Thermo-Redox

The detection principle of thermo-redox technology is based on the thermal decomposition of the explosive molecules and the subsequent reduction of the NO2 groups. Air containing the explosive sample is drawn into the system through an inlet at a flow of approximately 1.5 liters per minute. The air is then passed through a sample concentrator tube, which selectively adsorbs explosive vapor molecules using a proprietary coating on the tube's coils. The introduced sample is then pyrolyzed to release the NO2 group, which is then transferred to a membrane separator/sensor assembly. The membrane separator provides additional discrimination against potential chemical interferences. Then the gases are passed across the sensing surface of the detector and a small signal is generated.

Signals from the detector are collected, amplified, and delivered to the microprocessor, which determines the strength and time at which positive signals are obtained. The verification of explosive vapors is accomplished by comparing the strength of the signal from the detector with the time from the start of the analysis cycle. If both the signal strength and time requirements are met, a positive detection alarm results.

This detection system requires neither special carrier gases nor a radioactive source and is available in a relatively low cost ($23,000), handheld package. This technology lacks the ability to distinguish between specific types of explosives. In other words, an alarm could signal the detection of any of the detectable explosives, such as NG, TNT, many of the taggants, RDX, or PETN. Furthermore, thermo-redox cannot detect RDX and PETN by vapor sampling because of the very low vapor pressures of these compounds.

Field Ion Spectrometry (FIS)

Field ion spectrometry (FIS) is a new technology (less than 5 years old) that has been developed for trace detection of narcotics, explosives, and chemical warfare agents. This new technology incorporates a unique ion filter using dual transverse fields, which allows interferences to be electronically eliminated without the use of GC columns, membranes, or other physical separation methods.

FIS is related to ion mobility spectrometry in that it is a technique for separating and quantifying ions while they are carried in a gas at atmospheric pressure. In addition, both methods utilize soft ionization methods that yield spectra, in which the species of interest produce the main features.

In FIS, ions enter an analytical volume defined by a pair of parallel conducting plates where they execute two motions. The first is a longitudinal drift between the plates due to the bulk motion of a clean, dry carrier stream of air. The second is an oscillating motion transverse to the bulk flow velocity that occurs as the ions respond to an asymmetric, time-varying electric field imposed between the plates. In response to the asymmetric field, the ions tend to migrate toward one of the plates where they will be neutralized. A second DC field is simultaneously established across the plates and can be used to balance or compensate for the drift introduced by the primary field. The DC field intensity needed to compensate for the AC field induced drift depends on the mobility of the particular ion species under investigation, so that only specific ions can pass completely through the analytical volume and into the collection area for detection.

Therefore, the device can be tuned to selectively pass only the ions of interest. Scanning the DC field intensity produces a spectrum of ion current versus field intensity that is known as an ionogram.

In actual operation, the air sample to be analyzed is drawn directly into the sensor's ionizing cavity. Once ionized, analyte ions are electrically separated from the bulk sample and a steady flow of clean, dry air carries the ions through the spectrometer. All ions except those of interest are dispersed to the sensor's walls, permitting only a selected group to reach the detector. The ionogram recorded by sweeping the compensation voltage is similar to the output of a gas chromatograph or an ion mobility spectrometer.

The sensor has no moving parts except for a small recirculation fan and no consumables except for the replaceable calibrator and gas purification filters. The size of the instrument is 0.8 cubic feet, excluding a computer for control and display. The sole manufacturer of the FIS has reported limits of detection in the low picograms for common explosives such as RDX, PETN, and TNT. In addition, a response time of 2 seconds for a single component and approximately 5 seconds for each additional component is advertised. To date, there are no independent test data available for the FIS.

The instrument's estimated selling price is $20,000 for a single component analyzer, plus an additional $1,000 per extra component.

Mass Spectrometry (MS)

Mass spectrometry (MS) is mentioned here as a trace detection technique because it has been shown to be a very powerful analytical laboratory tool for explosives detection, even though it is not commercially available specifically for that use. In particular, its strength is low to sub-picogram detection limits with unusually high specificity. Oak Ridge National Laboratory has done considerable research and development with tandem mass spectrometry and with interfacing the most efficient ionization source to a mass spectrometer system for explosives vapor detection. However, most of the MS work has been geared toward laboratory type analyses and operations, and thus the system is quite complex and not field deployable.

More recently, several companies have advertised portable systems based on mass spectrometry, such as GC/MS, which can provide analysis in the lab or on the road. These systems can provide extensive analysis of air, gas, soil, solid, liquid, and water samples. However, these instruments are quite complex and relatively expensive, and they are not designed specifically for explosives detection. Furthermore, typical analysis cycle times are several minutes, as opposed to seconds, as with some of the other trace detection systems.

Sampling Techniques for Explosives Trace Detection Equipment

The explosives trace detection systems using the previously described detector technologies all require or utilize similar techniques in sampling. Trace detection sample acquisition can be accomplished either by vapor sampling or by swiping a surface to collect a particulate sample.

Most commercially available explosives detectors use a portable "dustbuster" type air vacuum for vapor sampling. Depending on the brand of instrument, the sampling filter that is placed in the vacuum may be either Teflon®, fiberglass, specially treated paper, or some kind of special fabric. No matter what material is used, the general idea is to pull air through the sampling medium, trapping the explosive molecules on the filter. Then the sampling medium is removed from the vacuum and placed in the detector for thermal desorption and subsequent analysis. Considerable research has been invested in determining the optimal airflows and the ideal filter material for the various commercially available explosives detection systems.

The second method of sampling afforded by most of the explosives detection systems is particulate or swipe sampling. Given the fact that a single particle can contain a microgram or more of explosive material, swiping the suspect surface can yield a much larger sample than vacuuming for a vapor sample. This is why all the manufacturers recommend swipe sampling if at all possible. The typical procedure is to wipe the suspect surface with the supplied swipes using a glove to prevent contamination of equipment and other sampling media. Then the swipe is placed in the detector and heated to evolve the trapped explosives molecules. The materials used for these swipes are typically paper or cloth. One manufacturer uses a reusable metal screen for surface swiping. Most other systems recommend that once a detection has been made, the swipes should not be reused, but disposed of properly. Since the price of these swipes can range from $0.01 to $1 per swipe, depending on the manufacturer, cost may be a factor in determining the right system for a given application.

Trace Detection Personnel Portals

Several contraband explosives detection personnel portals are either in the prototype/testing stage or are commercially available at this time. All of these systems incorporate detectors that have been previously described, namely ion mobility spectrometry, electron capture detection, and fast gas chromatography/chemiluminescence. A brief description of each portal system follows.

Model 85 Entry Scan Portal

The Model 85 Entry Scan Mark II portal, manufactured by Ion Track Instruments (ITI), has been used by the Nuclear Regulatory Commission (NRC) for personnel screening in several of their facilities for the past 10 years. During operation, a large sample airflow is blown horizontally across the person or object being screened. The air drawn in on the intake side of the archway then passes through a perforated wheel trap where the explosive vapors are deposited. Two heaters then heat the wheel to desorb the explosive, which is carried to an electron capture detector (containing a 10 mCi Ni-63 source) by a flow of argon. As the wheel trap continues to rotate, it is cooled by a small fan, which completes the sampling cycle. The detection of an explosive is indicated by a digital meter reading and by an audible signal and red indicator light.

The ITI Model 85 has three modes of operation for explosives detection. The first is the high sensitivity mode requiring 12 seconds for a complete sample and analysis cycle. This is the most sensitive mode and is advertised to have a good sensitivity to TNT and EGDN. The second mode of operation is the fast mode, which has a 6-second cycle period that reduces the detection capability for low-vapor-pressure explosives substantially. Finally, the walk-through mode accomplishes screening without requiring the subject to remain under the archway. Some problems in alarm resolution have been encountered in this mode since the alarm does not sound until 5 seconds after the subject has exited the portal.

This system is the oldest of the commercially available portal systems. The ITI Model 85 has good sensitivity to dynamite and several of the proposed taggants. This system, however, was not designed to detect the low vapor pressure compounds such as RDX- and PETN-based explosives. The system requires pure argon for operation and costs approximately $50,000.

SecurScan™ Portal

The SecurScan™ is a walk-through trace explosives detection system developed by Thermedics Detection, Inc. The SecurScan™ collects a sample as an individual walks through an array of wands fitted into the archway. The wands brush against the subject's body, vacuuming his or her clothing and removing any explosive vapor or particulate traces that may be present. After the sample has been collected, it is concentrated by filtering it from the high volume of air from the wands. The concentrated sample is then desorbed into the chemistry module where it is trapped for injection into the fast GC system and detected by chemiluminescence.

The SecurScan™ system can process people at the rate of 10 per minute. Several sensors have been engineered into the system to fully automate operation, including a CCD (charge coupled device) camera to help resolve alarms. To date, the SecurScan™ has undergone extensive laboratory evaluations and some airport testing. For further information on the test results, system availability, and pricing contact Thermedics Detection directly.

Federal Aviation Administration/Sandia National Laboratories Portal

A walk-through portal for the trace detection of contraband explosives is in its final stages of testing at Sandia National Laboratories. The portal is designed to screen personnel without any direct physical contact, and in this respect is similar to the metal detectors that are already widely used in airports and accepted by the general public. The airflow sampling utilized is capable of collecting explosives material in both vapor and particulate form, the latter being potentially present on the exterior of a person's clothing in the form of contamination.

Once a subject has entered the portal, air is blown down from the top of the portal and along the subject s body for 5 seconds and is collected at two slots at the base of the portal. At the same time, brief puffs of air are used to slightly ruffle the subject's clothing to aid in dislodging particulate, which may contain explosive molecules. The air then flows into a preconcentrator, which is essentially a molecular filter, allowing air to pass through to be exhausted while collecting heavy organic molecules such as explosives onto a screen. The screen is then heated to desorb the collected explosive molecules back into the gas phase, and the resulting explosives-enriched air is then pulsed into an IMS for detection. Two identical preconcentration/IMS detection systems, one in front and one in back, are used to sample the front and back side of the subject.

The Sandia portal is fully automated and has undergone extensive laboratory testing to fine tune its responses to some of the lower vapor pressure explosives. The system is currently scheduled for airport testing in September 1997. No information on system availability or cost can be given at present. Please contact Sandia National Laboratories, Department 5848, for more information.

ORION Walk-Through

CPAD Technologies, Inc., a Canadian company specializing in chemical detection systems, has developed the ORION Walk-Through explosives detection portal. The portal system consists of a stand-alone portable detector system based on gas chromatography/ion mobility spectrometry and a detachable personnel booth.

A gentle stream of air passes from toe to head as a person walks through the open booth. The system can be discretely incorporated into existing architecture or openly displayed as a deterrent. The GC/IMS detector plugs into the sampling booth when needed for personnel portal screening, or it can stand alone for other explosives trace detection applications. CPAD reports that the ORION detection system can detect EGDN, NG, AN (ammonium nitrate), TNT, RDX, and PETN in the picogram to nanogram range. (Also, as an option the system can detect the International Civil Aviation Organization [ICAO] taggants, i.e., DMNB [dimethylnitrobenzene], OMNT [ortho-mononitrotoluene], and PMNT [para-mononitrotoluene]). Typical analysis time for all detectable compounds is 10 seconds. Note that the sensitivity and explosives detected are for the basic detector system, the ORION, not the ORION Walk-Through. The portal detection limits may well be different than those quoted for the ORION detector only. Contact CPAD Technologies for more information on availability, system owners, and cost.

Since the development of explosives trace detection systems is moving so rapidly, manufacturers should be contacted about the latest product specifications and pricing early in any decisionmaking process.

Several of the trace detection systems mentioned in this report have been evaluated at Sandia National Laboratories to determine various operational and performance capabilities through funding by the Department of Energy (DOE). Results of these tests are beyond the scope of this report but are available upon request. Please contact the authors of this report for more information."

Biological Warfare Agents

As recently as 1998, the only biological warfare agent detection systems, point and standoff, used by the U.S. Army were the Biological Integrated Detection System (BIDS) and the XM-94 standoff Laser. Frost & Sullivan, Market Engineering Measurement Analysis of the World Chemical and Biological Warfare Agent Detector Market, 1998. Development of BIDS, which is actually a suite of instruments including a flow cytometer, mass spectrometer, microilluminometer, and Smart Ticket (by New Horizons Diagnostics, Inc.), was proven to be capable of detecting a variety of pathogens in about five minutes. Frost & Sullivan, supra.

Commercially available systems as of the time of filing the application for this patent include the Biological Aerosol Warning System (BAWS), and Joint Biological Point Detection System (JBPDS), both available from Lockheed Martin Librascope, Glendale, Calif. Also available is the 4WARN Real-time Integrated Biological & Chemical Agent Detection System, available from Computing Devices Canada (a General Dynamics Company), Ottawa, Ontario, Canada.

Presently, there are two basic classes of biological warfare agent detectors; immuno assay (antibody) devices, of which there are many different types (including flow cytometers); and nucleic acid techniques. In one such DNA technique, ultraviolet light is shone on proteins, which fluoresce at approximately 350 nm. DNA amplification techniques enable detection and identification of the organism. Perhaps future detectors will be developed to take advantage of the results of the Human Genome Project. In one such project at Argonne National Laboratory, funded by DARPA, biological microchips are developed which comprise glass or silicon wafers on which different substances are chemically immobilized. These substances are antibodies and short strands of DNA called oligonucleotides which bind, or hybridize, to any complementary DNA strands in the sample being tested. Then a specially-designed microscope detects where the DNA hybridized. A computer then analyzes the data and identifies the sample.

Weapons and Metals

Weapons and metals are conventionally detected with metal detectors and x-ray machines, used independently or in combination.

Metal detectors transmit low intensity magnetic fields that interrogate metal objects that pass through them. A transmitter generates the magnetic field that reacts with the metal objects in its field and a receiver measures the response from this reaction. There are two basic types of metal detectors: pulse induction and continuous wave. Pulse induction detectors typically have a transmitter panel and a receiver panel with a cross piece that separates them. Pulses of magnetic energy are repetitively generated by the transmitter and pass through the person or object being screened to the receiving panel. When passing through a multiple sensor continuous-wave detector, the person being screened is scanned from both sides by a continuously oscillating magnetic field. Transmitter elements and receiver sensors are installed in both side panels. In both systems, the transmitted magnetic fields induce a flow of eddy currents within the surface of metal objects. As eddy currents flow through the surface of a metal object they produce their own magnetic flux. These magnetic fields are formed in a manner analogous to those produced when a current exists through an electrical conductor. These magnetic fields are converted to electrical signals, which are then analyzed by a computer or microprocessor. The end result is, hopefully, an indication of the type of object sensed. Metal detectors are well known in the art, and a complete description of their theory and operation can be found at http://www.mscosales.com/rangersecurity2000/book2/, incorporated herein by reference.

Conventional x-ray devices and methods are disclosed in U.S. Pat. Nos. 5,692,446; 5,930,326; 5,838,758; and 5,692,029, all of which are incorporated herein by reference.

Nuclear Weapons and Materials

The most common detector for nuclear weapons and radioactive materials is the Geiger counter. Geiger counters are devices that detect and measure ionizing radiation emitted by radioactive sources. The heart of a Geiger counter is the Geiger-Mueller-Tube. This is a gas-filled tube, to which a voltage of several hundred volts is applied. Normally, the gas insulates and no current is drawn. When a radiation particle or quantum passes the tube, it triggers a gas discharge. The resulting current impulse is amplified and made either visible and/or audible (i.e., the familiar "clicking". Other well-known radiation detectors include dosimeters, and survey instruments (including ion chamber survey meters).

Detectors in the Patent Art

Detection methods and apparatus are documented in the patent art, although no one has apparently yet invented/patented a detection system for detecting a plurality of threats/agents as in the present invention.

U.S. Pat. No. 5,915,268 (Linder et al.) disclose a vertical flow chemical detection portal for screening objects or persons for trace amounts of chemical substances such as illicit drugs or explosives. The patent teaches the use of an ion mobility spectrometer as the detection device in a preferred embodiment, and also teaches the use of an electron capture device, gas chromatograph, chemiluminescense, mass spectrometer and Thermo-Redox as alternatives, all of which detect certain chemical and/or explosive agents. There is no teaching or suggestion in the patent of detecting any other agents, such as weapons or biological warfare agents.

U.S. Pat. No. 5,311,166 (Frye) discloses a security vestibule having a motion detector to sense the presence of an intruder, means for warning the intruder, and deterrent means (such as hot water, foul scented substances or dye) to discourage entry. The patent contains no teaching of chemical, biological or weapon detection.

U.S. Pat. No. 5,692,446 (Becker et al.) discloses a method and apparatus for detection of weapons using x-ray and metal detection technology. The patent does not teach detection of chemical or biological warfare agents.

U.S. Pat. No. 5,047,723 (Puumalainen) discloses an ion mobility sensor. Although the patent teaches the detection of "alien matter" in gas, there is no teaching in the patent of detecting chemical warfare agent, biological warfare agents, weapons and explosives.

U.S. Pat. Nos. 4,987,767 and 5,109,691 (Corrigan et al.) both teach explosives detection screening systems for the detection of explosives and other controlled substances such as drugs or narcotics. The patented inventions use vapor detection systems which may employ either a gas chromatograph or electron capture detector. The patents teach the detection of explosives and other controlled materials, but are silent as to biological warfare agents and weapons.

U.S. Pat. No. 6,073,499 (Settles) discloses a chemical trace detection portal based on the natural airflow and heat transfer of the human body. This patent teaches the existence of a human thermal plume and advocates and upward air flow stream in chemical/explosive detection portals. The patent further teaches the detection of chemicals, drugs and explosives, and mentions the need for screening for weapons, although no metal or x-ray detector is disclosed or suggested. The patent contains no teaching of detection schemes for biological warfare agents.

U.S. Pat. No. 5,692,029 (Husseiny et al.) discloses a detector for explosives and contraband that uses a portable (ATV) mounted x-ray detector, gamma ray detector and ultrasonic detector. The patent contains no teaching of biological warfare agent detection.

U.S. Pat. No. 5,866,430 (Grow) teaches a raman optrode process and device for detection of both chemicals and microorganisms. This patented device is designed to detect drugs, explosives, toxins, pathogens, biological sample constituents, and chemical and biological warfare agents. The patent contains no teaching of metal or weapon detection, or a teaching of a portal-type detection device.

U.S. Pat. No. 6,100,698 (Megerle et al.) teaches an improved ion mobility sensor and spectrometer having a corona discharge ionization source. Again, this patent contains no teaching or suggestion of detecting anything other than chemicals.

U.S. Pat. No. 5,965,882 (Megerle et al.) discloses a miniaturized ion mobility spectrometer sensor cell.

Clearly, then, there is a longfelt need for a "one-stop" physical security system for NBC-safe buildings that can nearly simultaneously detect the presence of weapons, explosives, chemical warfare agents, biological warfare agents, and/or radioactive materials or weapons on persons, in packages or in vehicles.

SUMMARY OF THE INVENTION

The present invention broadly comprises a method and apparatus for screening an object for the presence of an explosive, chemical warfare agent, biological warfare agent, drug, metal, weapon, and/or radioactive material. The apparatus includes a portal through which the object is arranged to pass, the portal including a housing equipped with an ion mobility spectrometer and a surface acoustic wave device for detecting explosives, drugs and chemical warfare agents. In another embodiment the housing is equipped with a biological warfare agent detector, chemical warfare agent detector, metal detector, x-ray system, and/or radiation detector.

The general object of the present invention is to provide a "one-stop" physical security system for NBC-safe buildings that can nearly simultaneously detect the presence of weapons, explosives, chemical warfare agents, biological warfare agents, and/or radioactive materials or weapons on persons, in packages or in vehicles.

These and other objects, features and advantages of the present invention will become readily apparent to those having ordinary skill in the art upon a reading of the following detailed description of the invention in view of the drawings and claims.

DETAILED DESCRIPTION OF THE PREFERRED EMBODIMENT

Figure 1:
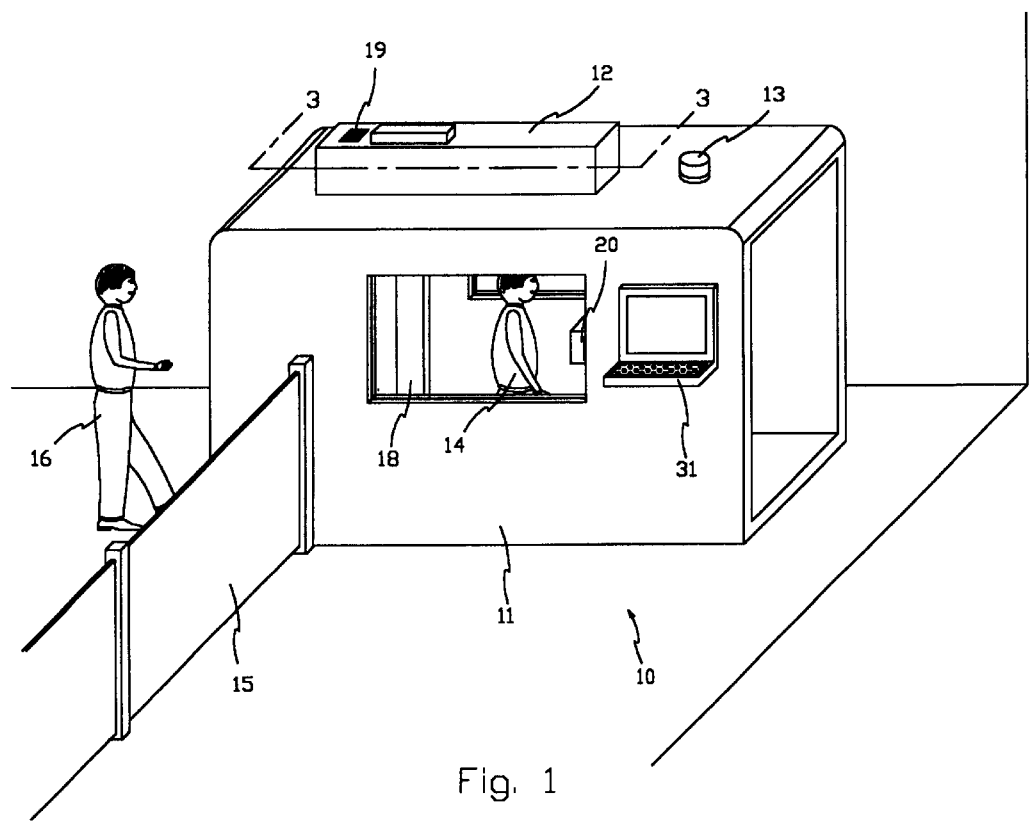
FIG. 1 is a perspective view of a first embodiment of the apparatus of the invention.

In the following detailed description of the preferred embodiment, and in the appended claims, the following terms are defined:

Biological warfare agent: refers generally to toxins, bioregulators, and biological warfare organisms.

Toxins: poisons produced by living organisms.

Bioregulators: substances related to those normally found in the body that regulate certain body functions and processes.

Biological warfare organisms: living organisms including viruses, bacteria, rickettsia, and fungi.

Chemical warfare agents: include, but are not limited to: blister agents (e.g., Mustards and Lewisite), nerve agents (e.g., Sarin, VX, Tabun and Soman)), arsenicals, the G-agents, and blood agents (cyanides).

Explosive includes explosives, blasting agents, and detonators. It further includes, but is not limited to those materials which are defined as explosive materials in section 841(c) of title 18, U.S.C.

Weapon: any object or substance designed to inflict a wound, cause injury, or incapacitate, including, but not limited to, all firearms, BB guns, air guns, pellet guns, knives (including switchblade knives), axes, hatchets, brass knuckles, swords, staffs, bos, ninja weapons, escrima sticks, sai, kama, whips, chains, shinai, tonfa, nunchaku, blowguns, slingshots, and cross-bows. It should be appreciated that this is only a partial list.

It should also be appreciated that, although the primary purpose of the present invention is to provide a security detection system, the detection system of the present invention will also detect the presence of drugs, in addition to threatening agents.

The present invention includes both a method and apparatus. The apparatus includes three embodiments. The first embodiment comprises a portal having a housing operatively arranged to screen a person for threatening agents. The second embodiment comprises a portal having a housing operatively arranged to screen vehicles for threatening agents. The third embodiment comprises a portal having a housing operatively arranged to screen packages for threatening agents. Although some sensors and detectors are common to all three embodiments, some are not, as will be described infra.

The first embodiment, for personnel, includes sensors for explosives, chemical warfare agents, radioactive materials, and biological warfare agents, in addition to metal detectors. All personnel entering a building who require screening are required to pass through the portal of this embodiment's apparatus, where all of the above classes of threats are detected.

The third embodiment, for packages, includes all of the sensors used to screen personnel, as well as x-ray sensors. The apparatus of this embodiment includes a conveyor for transporting the package through the portal housing.

The second embodiment, for vehicles, includes all of the sensors of the other two embodiments, except metal detectors. It should be appreciated that the drawings for these embodiments are not to scale. For example, although the apparatus for the second embodiment is shown large enough to screen an automobile, it should be apparent that the dimensions could be increased to screen larger vehicles, such as trucks.

Adverting now to the drawings, FIG. 1 is a perspective view of the apparatus of a first embodiment of the present invention. The apparatus broadly comprises a portal 10 having a housing 11 equipped with a variety of sensors arranged to detect and identify a variety of threatening agents. The apparatus shown is arranged to screen people for threatening agents. For example, person 14 is shown standing momentarily within the portal housing being screened, while person 16 is shown waiting his turn to be screened. Partition 15 prevents individuals from circumventing the portal. The portal includes a variety of sensors mounted in portal top-cap 12, which sensors are described in more detail infra. Mounted external to the portal housing is control panel 31, which may include an x-ray viewing screen. (X-ray detection is optional in this embodiment, since privacy issues may preclude x-ray detection for individuals in some circumstances or applications.) The portal also includes an alarm 13 which may comprise either an audio, visual or combination audio/visual alarm programmed to activate upon sensing of certain threats.

Figure 2:
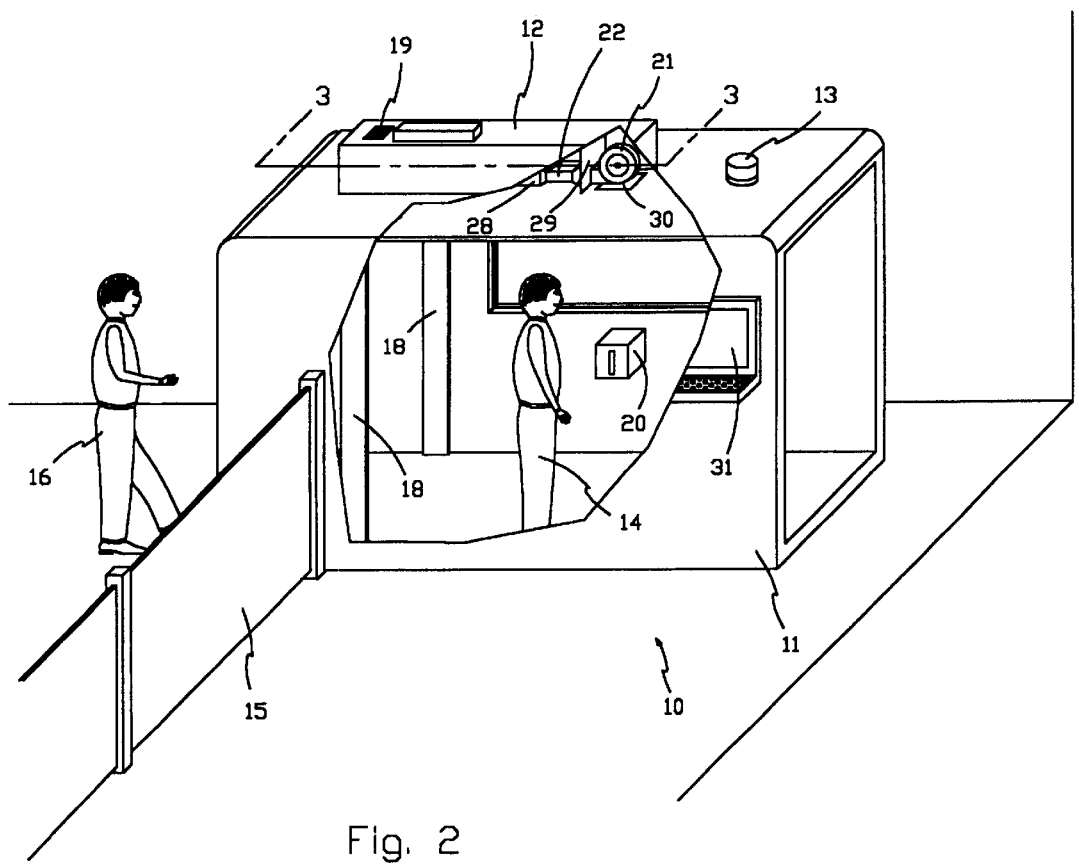
FIG. 2 is a view similar to that of FIG. 1, but with part of the portal housing cut away to show a person being screened for threatening agents.

FIG. 2 is a view similar to that of FIG. 1, but with a section of the portal housing cut away. This view shows metal detector 18, mounted within the housing, and Geiger counter 20 mounted on an internal housing wall. Both the metal detector and Geiger counter are well-known in the art, and both are described in more detail infra. The biological warfare agent, chemical warfare agent, and explosives sensors are all mounted in top-cap 12 of housing 11, although these sensors and their associated processing equipment could be mounted elsewhere. These sensors all operate on a principle of vapor and/or particulate sampling of the air surrounding the object being screened (so-called trace detection). In the case of a person, for example, it is known that all humans shed millions of microscopic skin cells daily, and that these cells, which may contain trace amounts of explosive or chemical warfare agents, migrate to the ambient air surrounding the person. In the embodiment shown, rotary blower 21 pulls air upwardly through the chamber via port 30 in the ceiling of the housing, and directs the sampled air to the array of sensors. Air jets, located in the floor of the housing, and not shown in the drawings, assist to create an airflow proximate the person being screened.

Figure 3:
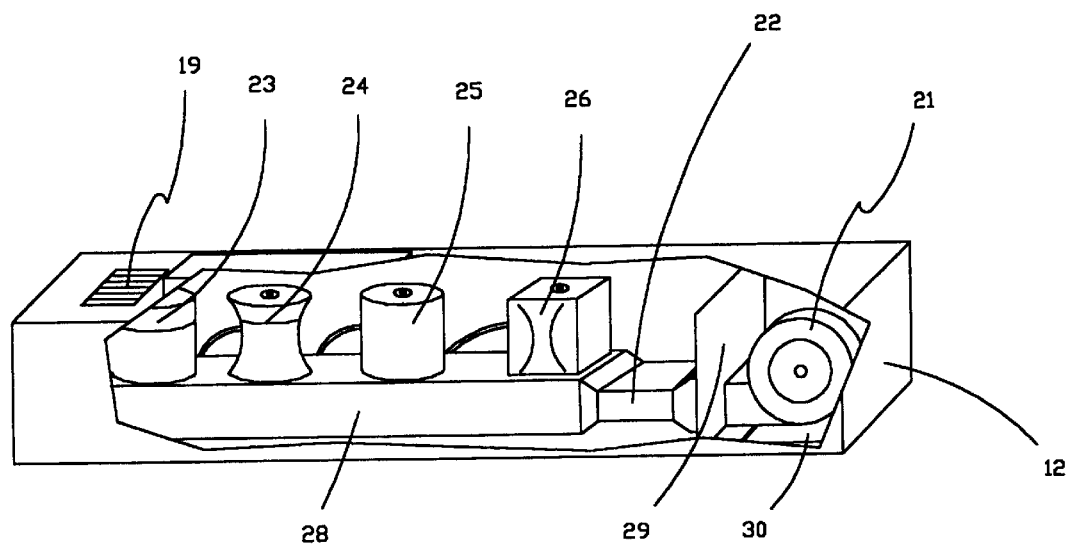
FIG. 3 is a view of the top of the portal housing taken along line 3—3 in FIG. 2.
Figure 4:
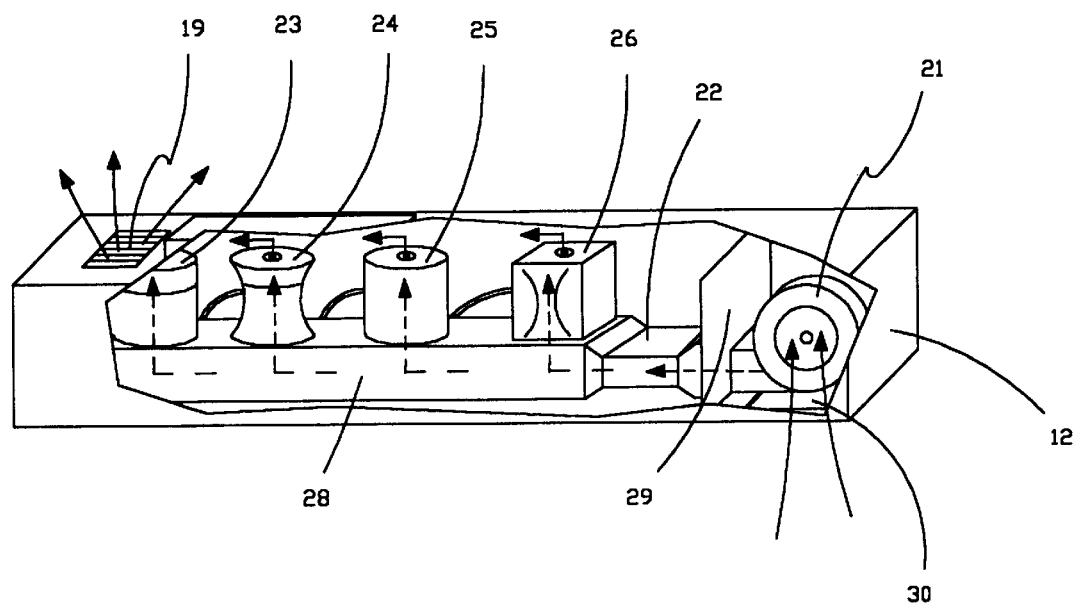
FIG. 4 is a view similar to that of FIG. 3, but showing air flow directed to some of the various sensors/detectors of the present invention.
Figure 5:
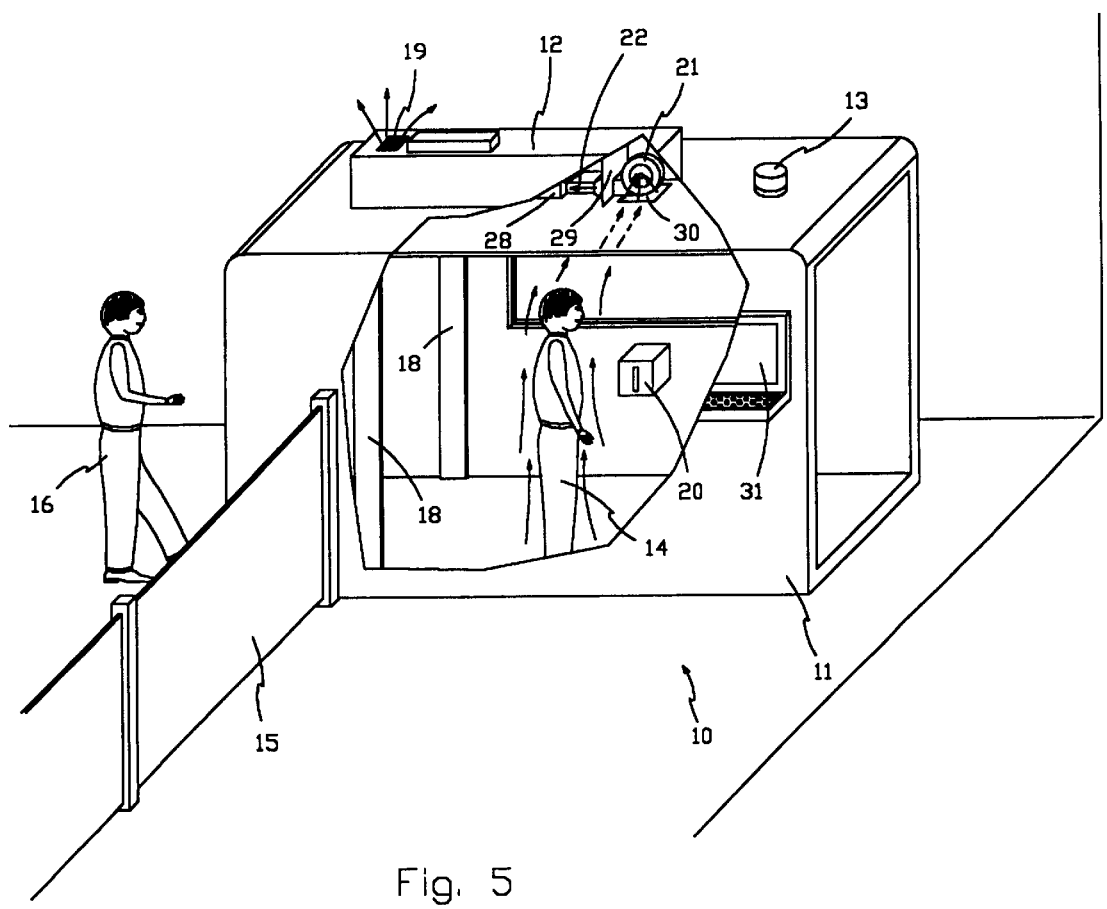
FIG. 5 is a view similar to that of FIG. 2, but showing air flow about the person being screened.
Figure 6:
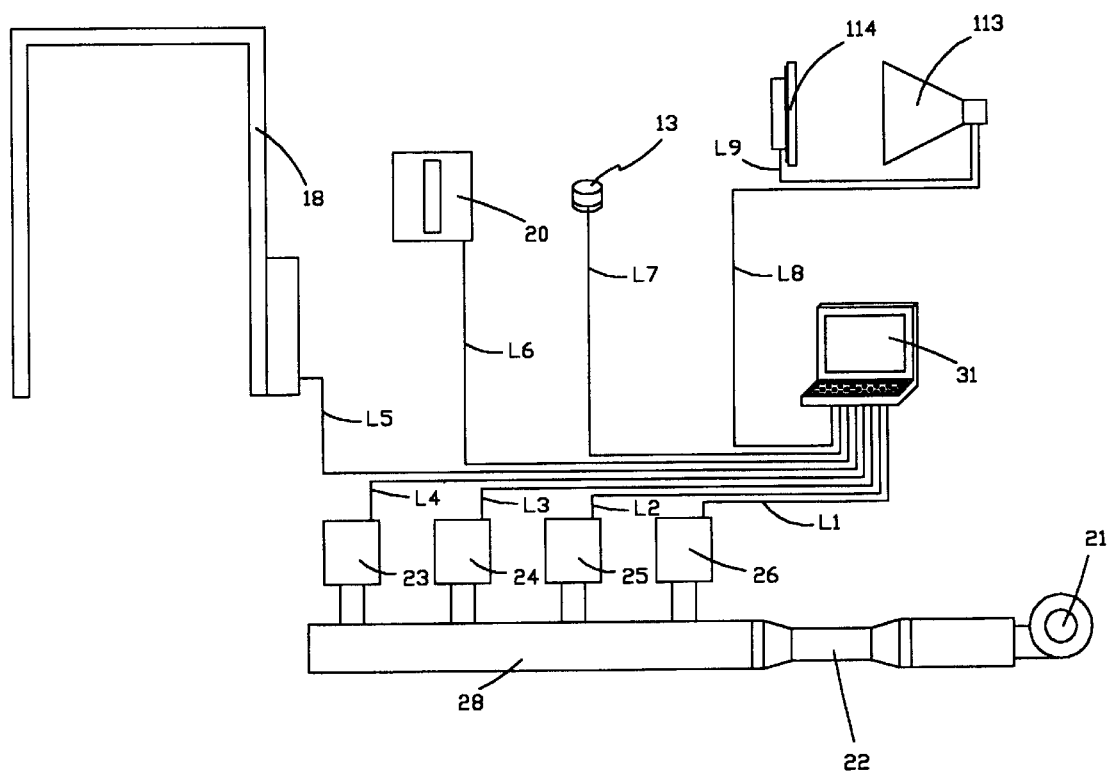
FIG. 6 is a general schematic diagram of the sensor network of the present invention.
Figure 7:
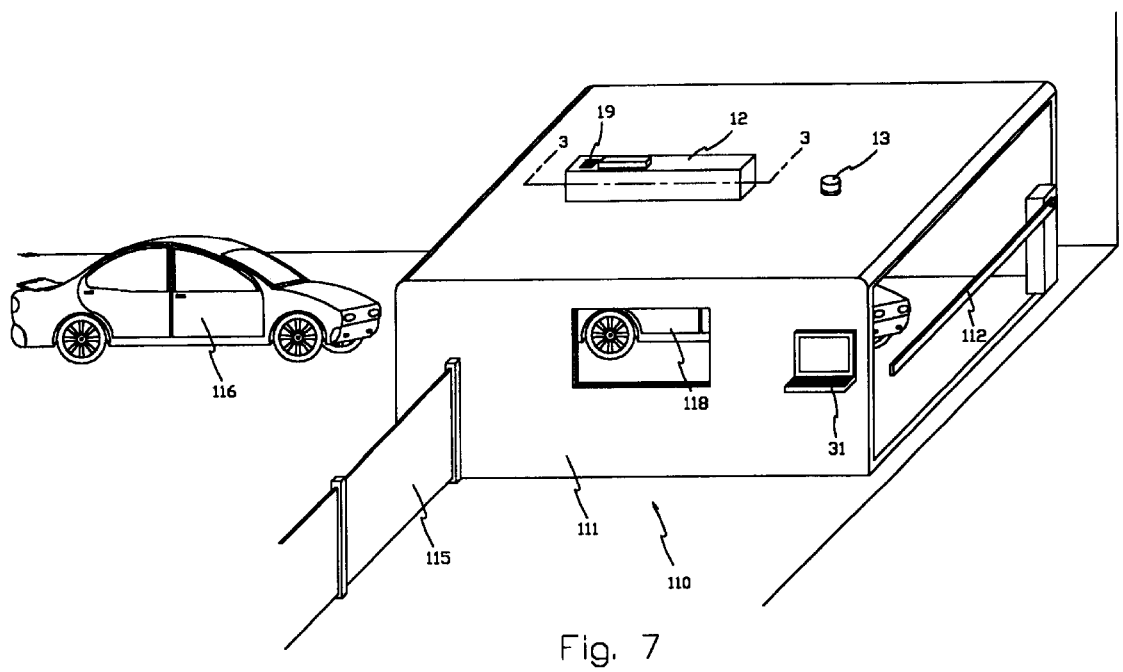
FIG. 7 is perspective view of a second embodiment of the apparatus of the present invention.
Figure 8:
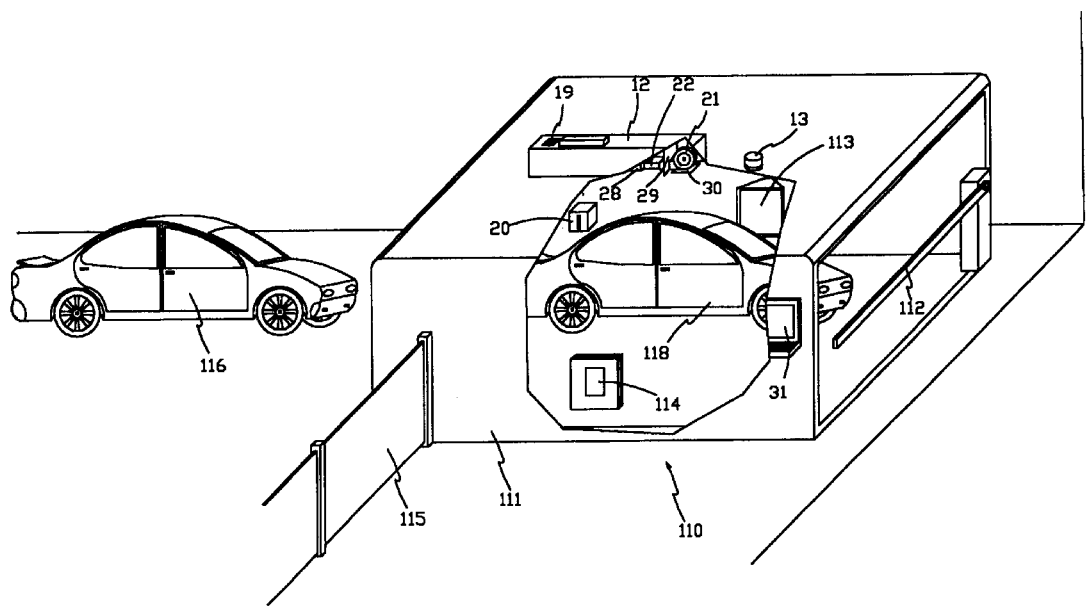
FIG. 8 is a view similar to that of FIG. 7, but with part of the portal housing cut away to show a vehicle being screened for threatening agents.

Top-cap 12 is shown in more detail in FIG. 3. The top-cap houses biological warfare sensors 23 and 24, and chemical/explosives sensors 25 and 26. In a preferred embodiment, sensor 25 is an ion mobility spectrometer operatively arranged to primarily detect explosives, and to secondarily detect chemical warfare agents, and sensor 26 is a surface acoustic wave device operatively arranged to secondarily detect and confirm explosives detected by the ion mobility spectrometer, and to primarily detect chemical warfare agents. The present invention is not limited to any specific ion mobility spectrometer or surface acoustic wave sensors. The ion mobility spectrometer sensors described in U.S. Pat. No. 6,100,698 (Megerle et al.), U.S. Pat. No. 5,965,882 (Megerle et al.), and U.S. Pat. No. 5,047,723 (Puumalainen), all of which are incorporated herein by reference, could be used in the present invention. The ion mobility spectrometer can also be of the type manufactured by Graseby Ionics, Ltd., Park Avenue, Bushey, Watford, Hertfordshire, England, or Environics Oy, Työmiehenkatu 2, 50100 MIKKELI, Finland. The theory and mechanics of operation of both ion mobility spectrometer sensors and surface acoustic wave sensors is described supra. In general, according to Graseby Ionics, Ltd., and PCP, Inc., "Ion mobility spectrometry (IMS) is a technique used to detect and characterize organic vapors in air. IMS involves the ionization of molecules and their subsequent temporal drift through an electric field. Analysis and characterization are based on analyte separations resulting from ionic mobilities rather than ionic masses; this difference distinguishes IMS from mass spectrometry. IMS operates at atmospheric pressure, a characteristic that has practical advantages over mass spectrometry, allowing a smaller analytical unit, lower power requirements, lighter weight, and easier use. These factors may facilitate use of IMS for mobile, field applications."http://www.clu-in.org/PRODUCTS/SITE/camp/graseby.html.

Figure 12:
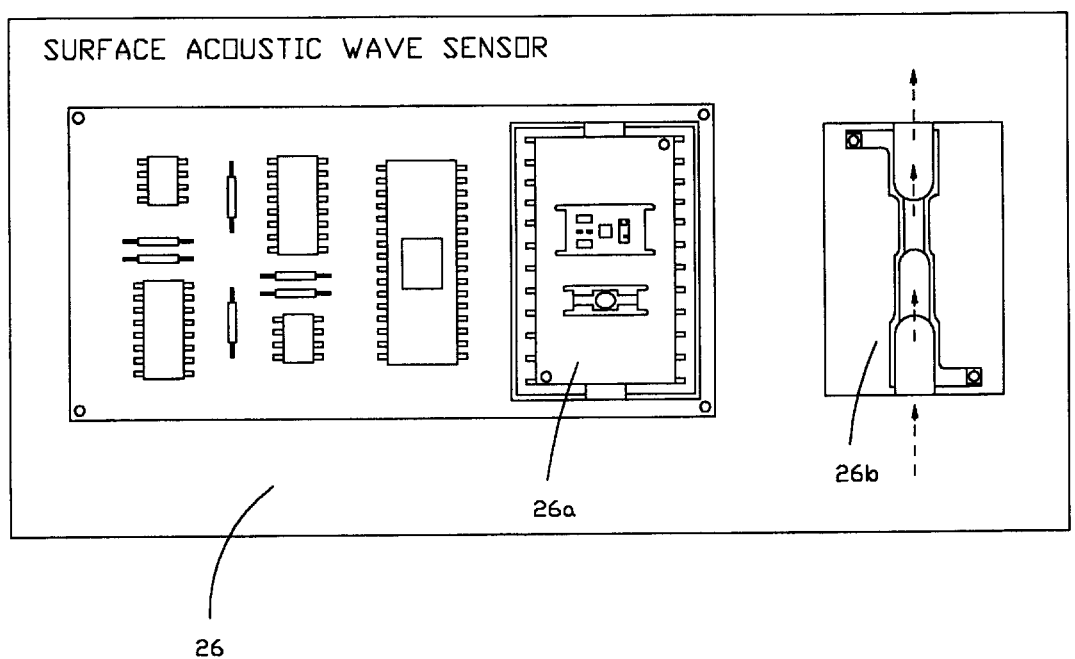
FIG. 12 is an illustration of one surface acoustic wave sensor used in the invention.
Figure 13:
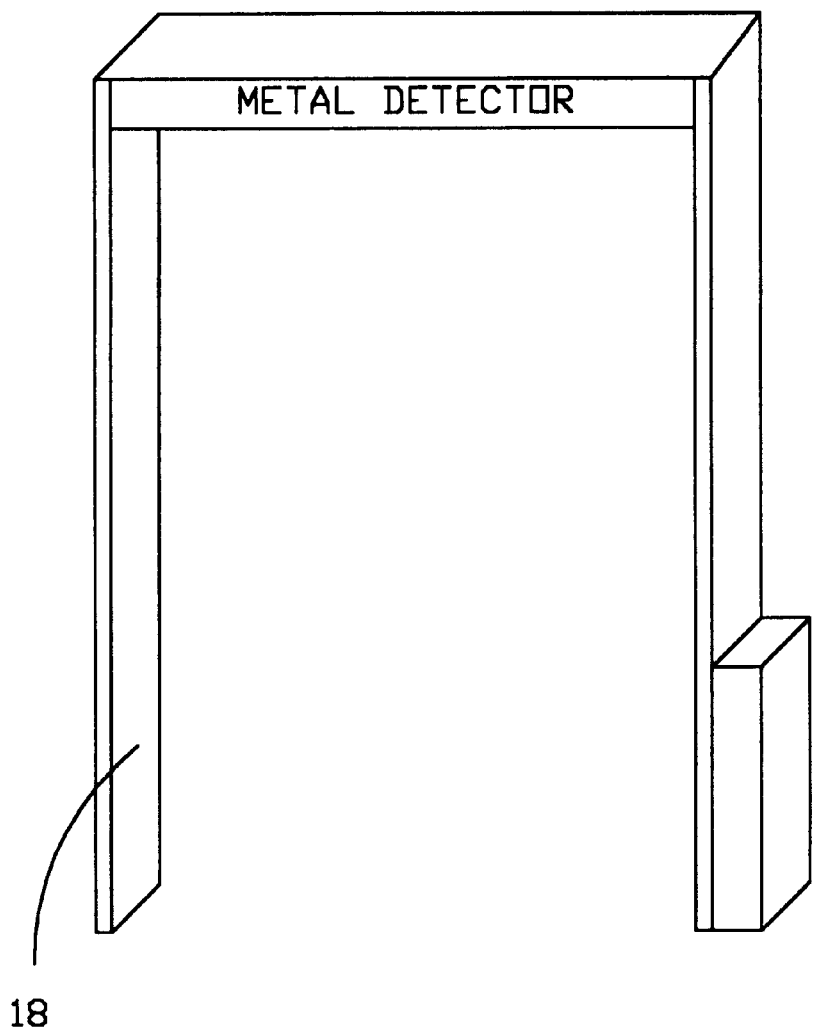
FIG. 13 is a perspective view of a metal detector used in the invention.
Figure 14A:
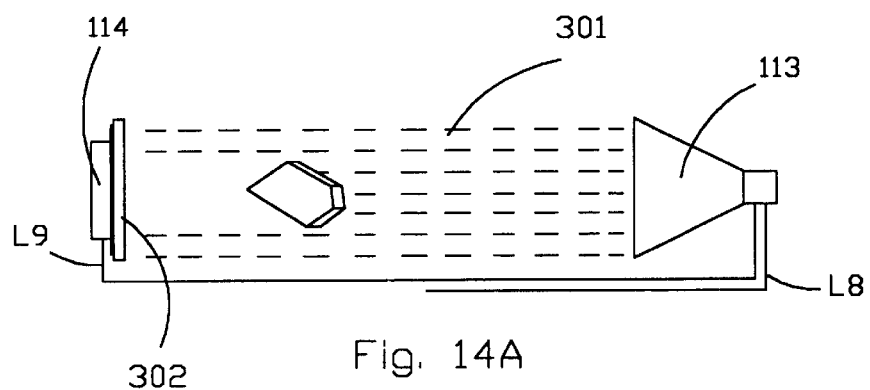
FIGS. 14A and 14B illustrate an x-ray device used in the invention.
Figure 14B:
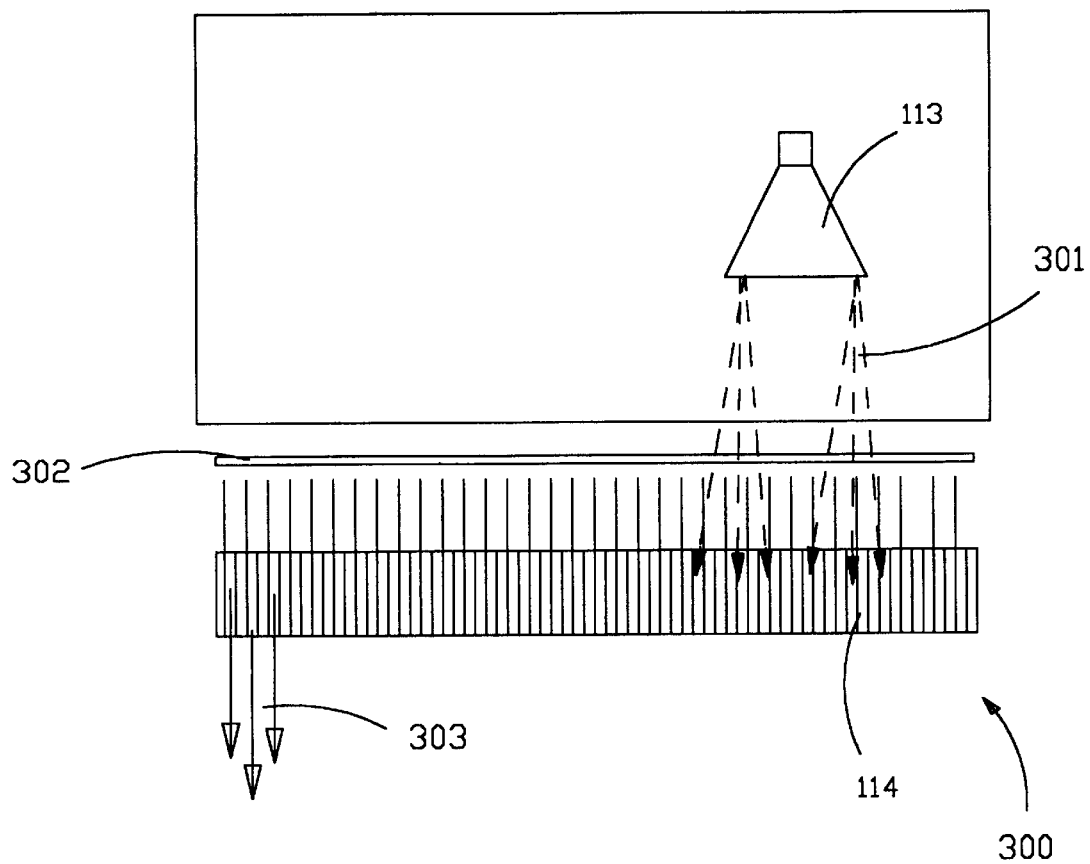
Figure 15:
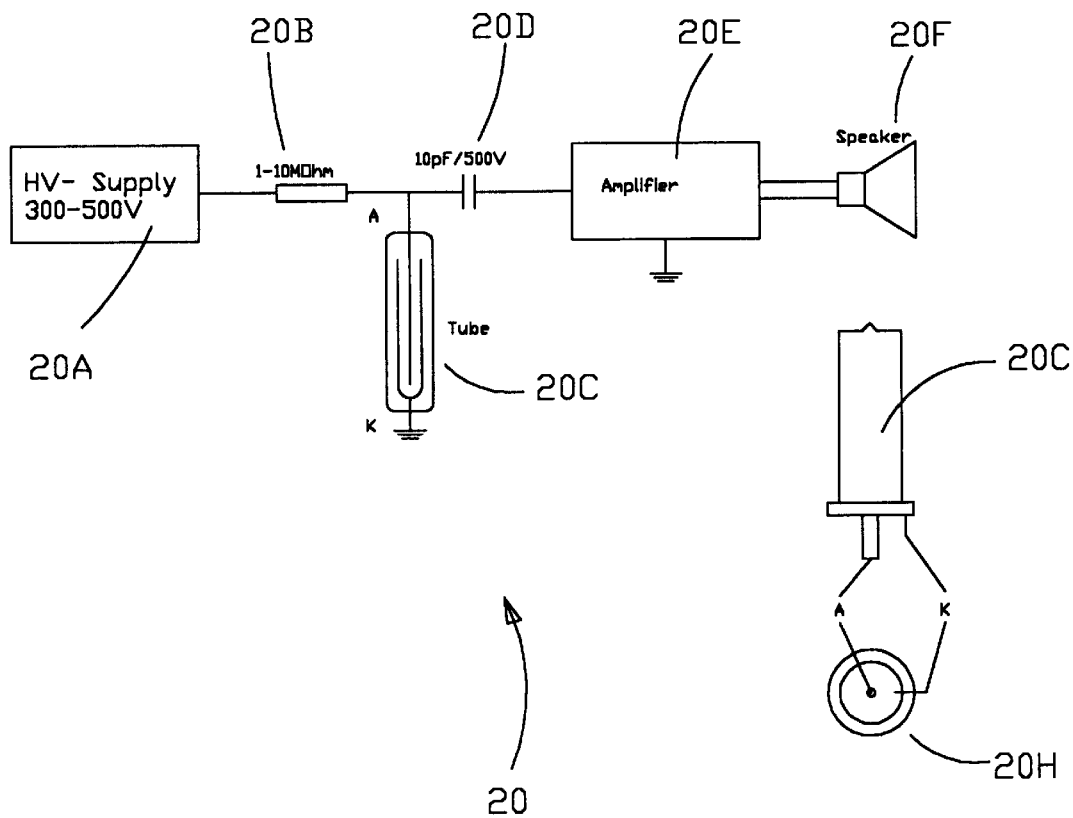
FIG. 15 illustrates a representative simple circuit for a Geiger counter used in the invention.

The present invention is not limited to any specific surface acoustic wave sensor 26. Surface acoustic wave sensor 26 may be of a type manufactured by Sawtek Incorporated of Orlando, Fla., or be of a type similar to the micro chemlab-on-a-chip of Sandia National Laboratories. The theory of operation of surface acoustic wave sensors is described supra (in the Background of the Invention), and an illustration of a surface acoustic wave sensor appears in FIG. 12. The actual sensor is labeled 26a in the drawing—the other components are associated electronics. The sensor shown in this drawing includes a novel RAM-air collector 26b, the subject of pending U.S. patent application Ser. No. 09/969, 196, filed Oct. 1, 2002, entitled "RAM-Air Collector for a Surface Acoustic Wave Sensor", which application is incorporated herein by reference.

Figure 11:
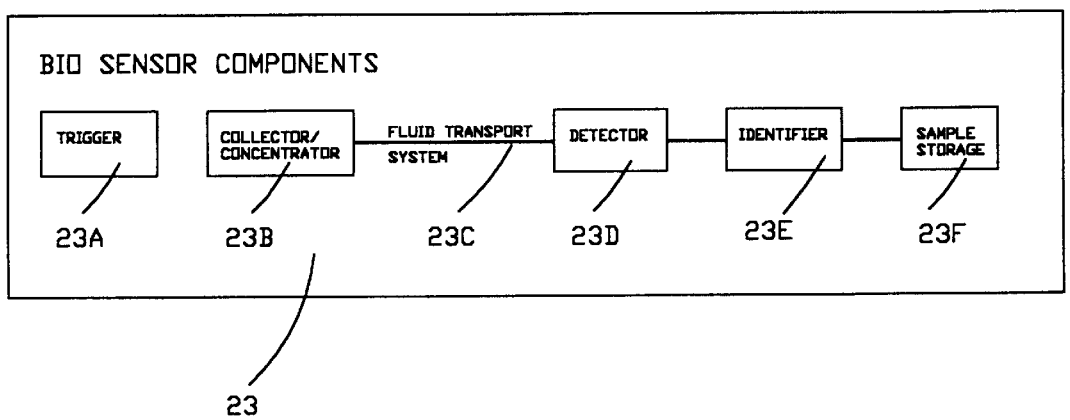
FIG. 11 is a general block diagram of a typical biological warfare agent sensor used in the invention.

In a preferred embodiment, the present invention includes two biological warfare agent sensors 23 and 24. It is preferred that a fast, near real-time sensor like the MIT Lincoln Laboratories BAWS III, or a similar sensor be used. Other possible sensors include the JBPDS (Joint Biological Point Detection System) available from Lockheed Martin Librascope, 811 Sonora Ave., Glendale, Calif., or the BAWS (Biological Aerosol Warning System), also available from Lockheed Martin Librascope (A block diagram of the major JBPDS sensor components is shown in FIG. 11).

In a preferred embodiment, first biological warfare sensor 23 detects the presence of particles containing proteins (using UV fluorescence) to detect the aromatic amino acids phenyl alanine, tyrosine, and tryptophane as well as other biological molecules, and to confirm that these particles were grown in growth medium and are therefore not of human or casual origin, and second sensor 24 to identify the biological warfare agent or biological material that is used in the manufacture of biological warfare agents. All biological materials will fluoresce under UV radiation, since they contain fluorescent species—aromatic amino acids and NADH. Furthermore, studies have shown that it is possible to distinguish naturally occurring biological materials from organisms that have been cultured in growth media, from certain, highly characteristic elements of the UV fluorescence spectra. The latter organism types are those that would be selected by those preparing weaponized biological warfare agents for an attack.

Second sensor 24 can be of the JPBDS type listed above, or the 4WARN sensor available from Computing Devices Canada Ltd. (a General Dynamics Company), 3785 Richmond Road, Ottawa, Canada K2H 5B7. The second sensor could, alternatively, be one of the SIMBAD identifying sensor modules, presently under development (see, e.g., http://www.arpa.mil/spo/programs/simbad.htm). The SIMBAD modules that could be used in this application include a micro surface enhanced laser Raman spectrometer coupled to a fluidic system that includes substrates with agent-specific binding molecules attached to those substrates under development by Biopraxis or as described in U.S. Pat. No. 5,866,430, incorporated herein by reference; a DNA sensor with in situ PCT amplification under development by Cepheid; a sensor using Micro IR laser-induced visible light fluorescence from up-converting phosphor particles that have attached to their surfaces; or a flow cytometer, similar to that being developed by Lawrence Livermore National Laboratories using a dye-containing, binding agent-covered capture and reporter bead chemistry being developed by Luminex. Since each of these identifying sensor modules is a liquid based assay, biological agents in the air blown onto the person's body are sampled by way of cyclone or rotary van air sampler, such as the BioCapture™ BT-550 or Bio-VIC Particles Concentrator made by MesoSystems Technology, Inc., 1021 N. Kellogg St., Kennewick, Wash. 99336.

Another type of biological warfare agent sensor that could be used is a PCR/Nucleic Acid Sensor. For example, Cepheid's Smart Cycler uses PCR for DNA amplification and Taqman methods for detecting the target DNA sequence. TaqMan methods involve special probes, about thirty nucleotides long, to which are bound a fluorophore (like FAM) and, generally two nucleotides away, a moiety that quenches the fluorescence of the fluorophore (like JOE). The oligonucleotide probe has a sequence complementary to a unique, targeted sequence in the DNA of a target agent.

During the PCR process, the target agent's DNA sequence is exposed when its two strands are separated during the denaturing step. During the annealing step the compatible oligonucleotide probe anneals with the target agent's DNA, even as the PCR primers are annealing to their target sequences on the same simplex DNA. During the extension step, when the complementary second strand is synthesized by the Thermus aquaticus DNA polymerase enzyme, the 5'-3' exogenase activity of this enzyme chops the Taqman probe into individual nucleotides, removing them from the host DNA. The fluorophore is bound to one of these separated and freed nucleotides, while the quencher is bound to another. They do not remain together in solution. The fluorophore is thus freed from its proximity to the quencher and can fluoresce in solution—and this is the only way that it can do so. The amount of fluorescence is a function of the amount of target DNA in solution, which increases as PCR amplification proceeds.

For this process to work, both PCR and Taqman annealing operations must function properly. Potential interference with, or suppression of, these processes by contaminants present in the air sample could represent a serious problem. The key question is, "Will a sensor module, based upon the Smart Cycler and its PCR/Taqman methods, work in the field, using practical samples collected in the normal way?" This is particularly an issue for a PCR-based sensor module, since it is known to be sensitive to certain environmental contaminants like divalent cations.

Figure 9:
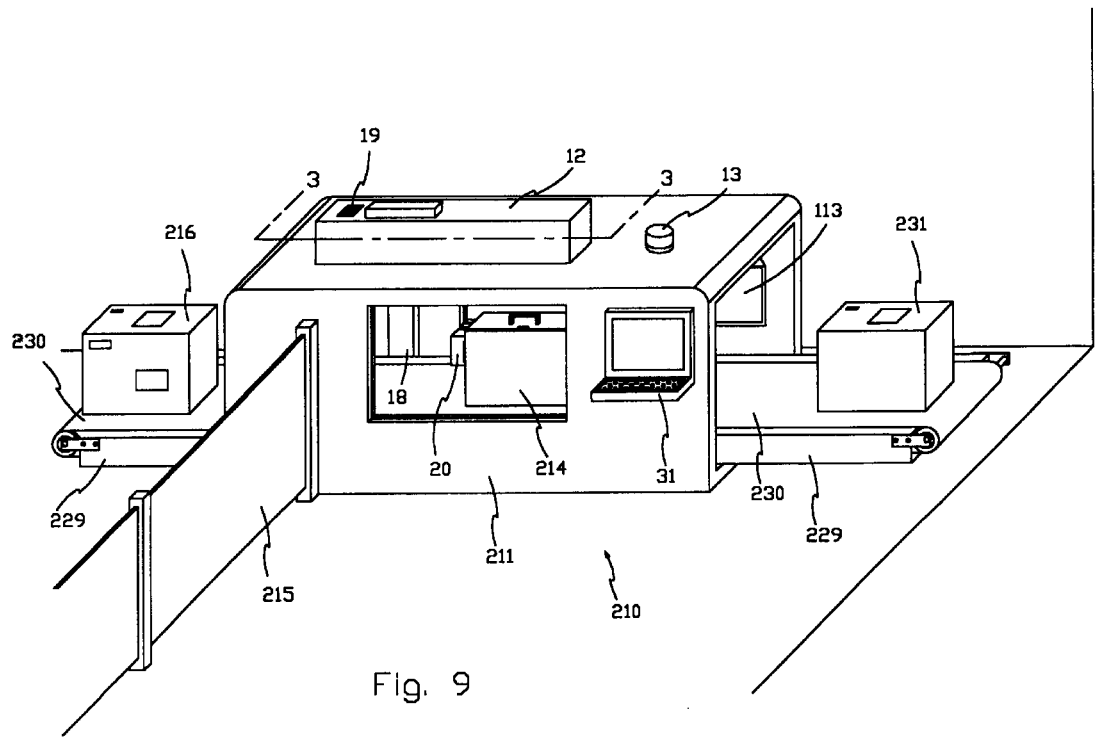
FIG. 9 is a perspective view of a third embodiment of the apparatus of the present invention.
Figure 10:
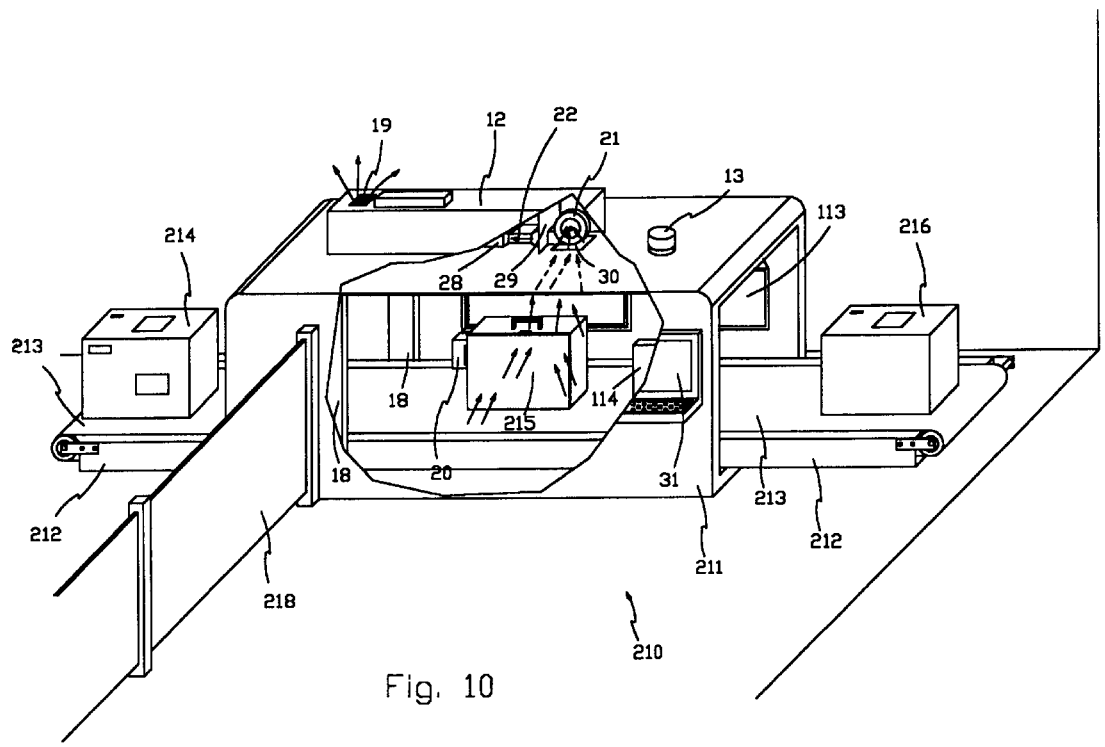
FIG. 10 is a view similar to that of FIG. 9, but with part of the portal housing cut away to show a package being screened for threatening agents.

I resolved to collect air samples inside a building using a commercial air sampler, spike them with an agent or agent simulant, and determine whether or not PCR amplification and Taqman identification would occur. I resolved not to do special cleaning of the air sampler fluid samples, even though such cleaning would be a part of an automated sensor module for obvious reasons, to provide a worst case scenario for the situation where the cleaning was not effective. These PCR amplifications with simultaneous DNA detection and identifications were performed by Cepheid on air sampler fluids collected by MesoSystems' air samplers inside their building near Kennewick, Wash., and spiked with B. anthracis spores. This work demonstrated that Cephid's methods work very well on practical air samples, and strongly support the use of this sensor module in an NBC-safe building sensor system.

Portal 10 also includes metal detector 18, shown in more detail in FIG. 13, which may be one of the CheckGate® detectors manufactured by Control Screening LLC, Fairfield, N.J., or the equivalent. Metal detectors are well known in the art as a means of weapon screening. Metal detectors suitable for this invention may use either the pulse induction or continuous wave technique. The metal detector of the present invention includes a transmitter that emits a low intensity magnetic field to interrogate metal objects that pass through the detector and its fields. The magnetic field reacts with any metal object in its field and a receiver measures the response from this reaction. Pulse induction detectors typically have a transmitter panel and a receiver panel with a cross piece that separates them. Pulses of magnetic energy are repetitively generated by the transmitter and pass through the person or object being screened to the receiver panel. When passing through a multiple sensor continuous-wave detector, the object being screened is scanned from both sides by a continuously oscillating magnetic field, and transmitter and receiver elements are in place in both panels. In both pulse induction and continuous wave, the transmitted magnetic fields induce a flow of eddy-currents within the surface of metal objects. As the eddy currents flow through the surface of a metal object they produce their own magnetic flux. Their magnetic fields are formed in a manner analogous to those produced when a current flows through an electrical conductor. The low intensity magnetic flux, including its disturbances due to detected metal, is converted to analog electrical signals, and then to digital signals for processing and analysis by a computer. Modern detectors provide a visual representation of the metal objects detected. A more complete description of the theory of metal detectors can be found at http://www.mscosales.com, although it should be appreciated that metal detectors are well known in the art.

The portal also includes Geiger counter 20, but may optionally include any suitable radiation detection device, such as a dosimeter or survey instrument. A typical well-known Geiger counter apparatus and circuit 20 is shown in FIG. 15.

Top-cap 12 houses both the chemical warfare agent and biological warfare agent sensors, as well as blower 21 and associated ductwork and equipment, as best shown in FIGS. 3 and 4. As best shown in FIG. 4, sampled air enters the top cap via inlet port 30, induced by blower 21. The air passes through diverter 29 into preconcentrator 22, and then into duct 28 to respective sensors 23, 24, 25 and 26. It should be appreciated that each individual sensor may have its own independent preconcentrator. For example, as described earlier, one of the bio-sensors may have a separate air sampler to accommodate the liquid based assay module of the sensor. Sampled air flow is indicated by arrows in FIG. 4. Exhaust air is vented to the ambient atmosphere via vent 19. As best shown in FIG. 5, the sampled air that enters the top-cap is forced upwardly from floor jets (not shown), which pass air over and proximate the person being screened, and is then induced into the top-cap sensing array via blower 21.

A schematic diagram illustrating the interconnection of the various sensors of the invention is shown in FIG. 6. It is seen here that the apparatus of the present invention broadly comprises metal detector 18, radiation detector 20, biological warfare agent detectors 23 and 24, chemical warfare agent detectors 25 and 26, and x-ray detector 113–114, although not all sensors are present in all embodiments of the present invention. The respective sensors are connected to controller 31, which may be a personal computer operatively arranged to receive communication from the respective sensors and to display information relative to agents being detected, and to indicate alarm conditions, either visual or audible, via alarm 13.

A second embodiment of the present invention is shown in FIG. 7. In this embodiment, the portal is large enough to screen large objects, such as vehicles. Portal 110 shown in FIG. 7 is large enough to screen automobiles, although it should be appreciated that even larger portals could be constructed to screen larger vehicles such as trucks and tractor-trailers. FIG. 8 is a view similar to that of FIG. 7, but with a section of the portal housing cut away to show vehicle 118 being screened. The sensors in this embodiment are the same as those in the first embodiment, with the addition of x-ray apparatus 113–114. Although a conventional x-ray apparatus is shown in the drawings, it should be appreciated that a side scatter tomography system could also be used, such as the one illustrated in FIGS. 14A and 14B, which apparatus is described in detail in U.S. Pat. No. 5,930,326. A side scatter system would require some modifications to the mounting of the apparatus, since the transmitter and receiver are at right angles to one another. This could be accomplished by mounting either the transmitter or receiver on a door of the portal housing, perpendicular to the side walls.

Air flow and sampling in this embodiment is also identical as in the first embodiment, although it is preferable to open the windows of the vehicle during screening, and additional air jets directed at the open windows may also be preferable. Once vehicle 118 has been screened, security barrier 112 raises to permit the vehicle to exit the portal, whereupon vehicle 116 may enter the portal for screening.

Yet a third embodiment of the invention is shown in FIG. 9. In this embodiment, portal 210 is equipped with a conveyor 229, operatively arranged to pass packages, such as packages 214 and 216, through portal housing 211 along conveyor belt 230 for screening. The drive motor of the conveyor is programmed to position the package to be screened at an optimal location within the housing, and to pause long enough for the screening to occur. Again, the sensors in this embodiment are identical in structure and operation as in the second embodiment, as is the air flow and sampling, as best shown in cut-away view in FIG. 10.

Thus, it is seen that the objects of the present invention are efficiently obtained, although modifications and changes to the invention should be readily apparent to those having ordinary skill in the art, and these modifications are intended to be within the spirit and scope of the invention as claimed.

What I claim is:

1. An apparatus for screening an object for the presence of an explosive, comprising:
    a portal through which said object is arranged to pass, said portal having a housing equipped with:
        an ion mobility spectrometer operatively arranged to primarily detect said explosive; and,
        a surface acoustic wave device operatively arranged to secondarily detect and confirm said explosive detected by said ion mobility spectrometer.

2. The apparatus recited in claim 1 further comprising a first biological warfare agent detector operatively arranged within said housing to screen said object for the presence of biological warfare agents.

3. The apparatus recited in claim 2 wherein said first biological warfare agent detector is operatively arranged to use ultraviolet fluoroescence to detect biological molecules.

4. The apparatus recited in claim 3 wherein said first biological warfare agent detector is operatively arranged to use ultraviolet fluorescence to detect phenyl alanine, tyrosine, and tryptophane.

5. The apparatus recited in claim 2 further comprising a second biological warfare agent detector operatively arranged to identify said biological warfare agent.

6. The apparatus recited in claim 5 wherein said second biological warfare agent detector comprises a micro surface enhanced laser Raman spectrometer including substrates with agent-specific binding molecules attached to said substrates.

7. The apparatus recited in claim 5 wherein said second biological warfare agent detector comprises a DNA sensor with in situ PCT amplifcation.

8. The apparatus recited in claim 5 wherein said second biological warfare agent detector comprises a sensor using micro IR laser-induced visible light fluoroescence from up-converting phosphor particles that have attached to surfaces of said particles.

9. The apparatus recited in claim 5 wherein said second biological warfare agent detector comprises a flow cytometer comprising dye-containing, binding agent-covered capture and reporter bead chemistry.

10. The apparatus recited in claim 5 further comprising means for collecting air samples associated with said object, where said air samples potentially contain said biological warfare agent.

11. The apparatus recited in claim 10 wherein said means for collecting said air samples comprises a cyclone blower/fan.

12. The apparatus recited in claim 10 wherein said means for collecting said air samples comprises a rotary blower/fan.

13. The apparatus recited in claim 10 further comprising means for concentrating air samples containing said biological warfare agent in fluid for further analysis.

14. The apparatus recited in claim 1 further comprising a metal detector housed in said housing and operatively arranged to screen said object for the presence of metal and weapons.

15. The apparatus recited in claim 1 further comprising an x-ray detector housed in said housing and operatively arranged to screen said object for a weapon.

16. The apparatus recited in claim 1 further comprising a radiation detector housed in said housing and operatively arranged to screen said object for radioactive material.

17. The apparatus recited in claim 1 wherein said object is a person.

18. The apparatus recited in claim 1 wherein said object is a package.

19. The apparatus recited in claim 1 wherein said object is a vehicle.

20. The apparatus recited in claim 1 further comprising means for creating air flow over said object and for sampling said air flow.

21. The apparatus recited in claim 1 wherein said ion mobility spectrometer is operatively arranged to primarily detect drugs, and said surface acoustic wave device is operatively arranged to secondarily detect drugs.

22. An apparatus for screening an object for the presence of a chemical warfare agent, comprising:
    a portal through which said object may pass, said portal having a housing equipped with:
        a surface acoustic wave device operatively arranged to primarily detect said chemical warfare agent; and,
        an ion mobility spectrometer operatively arranged to secondarily detect and confirm said chemical warfare agent detected by said surface acoustic wave device.

23. The apparatus recited in claim 22 further comprising a first biological warfare agent detector operatively arranged within said housing to screen said object for the presence of biological warfare agents.

24. The apparatus recited in claim 23 wherein said first biological warfare agent detector is operatively arranged to use ultraviolet fluoroescence to detect biological molecules.

25. The apparatus recited in claim 24 wherein said first biological warfare agent detector is operatively arranged to use ultraviolet fluoroescence to detect phenyl alanine, tyrosine, and tryptophane.

26. The apparatus recited in claim 23 further comprising a second biological warfare agent detector operatively arranged to identify said biological warfare agent.

27. The apparatus recited in claim 26 wherein said second biological warfare agent detector comprises a micro surface enhanced laser Raman spectrometer including substrates with agent-specific binding molecules attached to said substrates.

28. The apparatus recited in claim 26 wherein said second biological warfare agent detector comprises a DNA sensor with in situ PCR amplification.

29. The apparatus recited in claim 26 wherein said second biological warfare agent detector comprises a sensor using micro IR laser-induced visible light fluroescence from up-converting phosphor particles that have attached to surfaces of said particles.

30. The apparatus recited in claim 26 wherein said second biological warfare agent detector comprises a flow cytometer comprising dye-containing, binding agent-covered capture and reporter bead chemistry.

31. The apparatus recited in claim 26 further comprising means for collecting air samples associated with said object, where said air samples potentially contain said biological warfare agent.

32. The apparatus recited in claim 31 wherein said means for collecting said air samples comprises a cyclone blower/fan.

33. The apparatus recited in claim 31 wherein said means for collecting said air samples comprises a rotary blower/fan.

34. The apparatus recited in claim 31 further comprising means for concentrating air samples containing said biological warfare agent in fluid for further analysis.

35. The apparatus recited in claim 22 further comprising a metal detector housed in said housing and operatively arranged to screen said object for the presence of metal and weapons.

36. The apparatus recited in claim 22 further comprising an x-ray detector housed in said housing and operatively arranged to screen said object for a weapon.

37. The apparatus recited in claim 22 further comprising a radiation detector housed in said housing and operatively arranged to screen said object for radioactive material.

38. The apparatus recited in claim 22 wherein said object is a person.

39. The apparatus recited in claim 22 wherein said object is a package.

40. The apparatus recited in claim 22 wherein said object is a vehicle.

41. The apparatus recited in claim 22 further comprising means for creating air flow over said object and for sampling said air flow.

42. The apparatus recited in claim 22 wherein said ion mobility spectrometer is operatively arranged to primarily detect drugs, and said surface acoustic wave device is operatively arranged to secondarily detect drugs.

43. An apparatus for screening an object for a threatening agent, comprising:
a portal through which said object may pass, said portal having a housing equipped with:
a surface acoustic wave device operatively arranged to detect said threatening agent;
an ion mobility spectrometer operatively arranged to detect said threatening agent; and,
a biological warfare agent detector operatively arranged to detect said threatening agent.

44. The apparatus recited in claim 43 wherein said threatening agent is selected from the group consisting of explosives, drugs, chemical warfare agents, and biological warfare agents.

45. The apparatus recited in claim 43 wherein said portal housing further comprises a metal detector.

46. The apparatus recited in claim 43 wherein said portal housing further comprises an x-ray detection apparatus.

47. The apparatus recited in claim 43 wherein said portal housing further comprises a radiation detector.

48. An apparatus for screening an object for a threatening agent, comprising:
a portal through which said object may pass, said portal having a housing equipped with:
a chemical warfare agent detector operatively arranged to detect said threatening agent;
a biological warfare agent detector operatively arranged to detect said threatening agent; and,
a metal detector operatively arranged to detect said threatening agent.

49. The apparatus for screening an object for a threatening agent recited in claim 48 wherein said portal housing further comprises an x-ray detection apparatus.

50. The apparatus recited in claim 48 wherein said portal housing further comprises a radiation detector.

51. A method of screening an object for the presence of an explosive, comprising:
passing said object through a portal which houses a plurality of detectors;
sampling air which has passed over said object with an ion mobility spectrometer operatively arranged to primarily detect said explosive; and,
sampling air which has passed over said object with a surface acoustic wave device operatively arranged to secondarily detect and confirm said explosive detected by said ion mobility spectrometer.

52. The method recited in claim 51 further comprising the step of sampling air which has passed over said object with a biological warfare agent detector operatively arranged to detect and identify biological warfare agents.

53. The method recited in claim 52 further comprising the step of x-raying said object.

54. The method recited in claim 53 further comprising the step of subjecting said object to a metal detector.

55. The method recited in claim 54 further comprising the step of subjecting said object to a radiation detector.

56. A method of screening an object for the presence of a chemical warfare agent, comprising:
passing said object through a portal which houses a plurality of detectors;
sampling air which has passed over said object with a surface acoustic wave device operatively arranged to primarily detect said chemical warfare agent; and,
sampling air which has passed over said object with an ion mobility spectrometer operatively arranged to secondarily detect and confirm said chemical warfare agent detected by said surface acoustic wave device.

57. The method recited in claim 56 further comprising the step of sampling air which has passed over said object with a biological warfare agent detector operatively arranged to detect and identify biological warfare agents.

58. The method recited in claim 57 further comprising the step of x-raying said object.

59. The method recited in claim 58 further comprising the step of subjecting said object to a metal detector.

60. The method recited in claim 59 further comprising the step of subjecting said object to a radiation detector.

* * * * *

UNITED STATES PATENT AND TRADEMARK OFFICE
CERTIFICATE OF CORRECTION

PATENT NO. : 6,610,977 B2 Page 1 of 1
DATED : August 26, 2003
INVENTOR(S) : Clifford Megerle It is certified that error appears in the above-identified patent and that said Letters Patent is hereby corrected as shown below:

<u>Column 24,</u>
Line 36, please replace "PCT" with -- PCR --
Line 48, please replace "PCT amplifcation" with -- PCR amplification --

Signed and Sealed this

Seventh Day of October, 2003

JAMES E. ROGAN
*Director of the United States Patent and Trademark Office*